(12) United States Patent
Stoessel et al.

(10) Patent No.: US 8,999,521 B2
(45) Date of Patent: Apr. 7, 2015

(54) MATERIALS FOR ORGANIC ELECTROLUMINESCENT DEVICES

(75) Inventors: Philipp Stoessel, Frankfurt am Main (DE); Holger Heil, Darmstadt (DE); Amir Parham, Frankfurt (DE); Horst Vestweber, Gilserberg (DE)

(73) Assignee: Merck Patent GmbH, Darmstadt (DE)

( * ) Notice: Subject to any disclaimer, the term of this patent is extended or adjusted under 35 U.S.C. 154(b) by 1021 days.

(21) Appl. No.: 12/294,180

(22) PCT Filed: Feb. 28, 2007

(86) PCT No.: PCT/EP2007/001732
§ 371 (c)(1),
(2), (4) Date: Sep. 23, 2008

(87) PCT Pub. No.: WO2007/110129
PCT Pub. Date: Oct. 4, 2007

(65) Prior Publication Data
US 2009/0146139 A1    Jun. 11, 2009

(30) Foreign Application Priority Data
Mar. 24, 2006 (DE) .......................... 10 2006 013 802

(51) Int. Cl.
| | | |
|---|---|---|
| H01L 51/00 | (2006.01) | |
| H01J 1/62 | (2006.01) | |
| C07C 43/275 | (2006.01) | |
| C07C 13/567 | (2006.01) | |
| C07C 15/28 | (2006.01) | |
| C07C 15/52 | (2006.01) | |
| C07C 211/54 | (2006.01) | |
| C07C 211/56 | (2006.01) | |
| C07C 211/58 | (2006.01) | |
| C09K 11/06 | (2006.01) | |
| H05B 33/14 | (2006.01) | |
| H01L 51/50 | (2006.01) | |

(52) U.S. Cl.
CPC ............. *C07C 43/275* (2013.01); *C07C 13/567* (2013.01); *C07C 15/28* (2013.01); *C07C 15/52* (2013.01); *C07C 211/54* (2013.01); *C07C 211/56* (2013.01); *C07C 211/58* (2013.01); *C09K 11/06* (2013.01); *H01L 51/0052* (2013.01); *H01L 51/0058* (2013.01); *H01L 51/006* (2013.01); *H05B 33/14* (2013.01); C09K 2211/1011 (2013.01); H01L 51/0071 (2013.01); H01L 51/0072 (2013.01); H01L 51/0094 (2013.01); H01L 51/5012 (2013.01); H01L 51/5048 (2013.01); Y02E 10/549 (2013.01); Y10S 428/917 (2013.01)

(58) Field of Classification Search
CPC ...... C07C 13/567; C07C 15/28; C07C 15/52; C07C 211/54; C07C 211/56; C07C 211/58; C07C 43/275; C09K 11/06; C09K 2211/1011; H01L 51/0052; H01L 51/0058; H01L 51/006; H01L 51/0071; H01L 51/0072; H01L 51/5012; H01L 51/5048; H05B 33/14; Y02E 10/549

See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,840,217 A | 11/1998 | Lupo et al. | |
| 5,935,721 A | 8/1999 | Shi et al. | |
| 5,968,675 A * | 10/1999 | Tamano et al. | 428/690 |
| 6,458,909 B1 | 10/2002 | Spreitzer et al. | |
| 6,534,199 B1 | 3/2003 | Hosokawa et al. | |
| 6,713,192 B2 | 3/2004 | Fukuoka et al. | |
| 6,878,469 B2 * | 4/2005 | Yoon et al. | 428/690 |
| 6,908,783 B1 | 6/2005 | Kuehl et al. | |
| 7,485,733 B2 | 2/2009 | Kim et al. | |
| 7,604,874 B2 | 10/2009 | Kim et al. | |
| 2002/0132134 A1 * | 9/2002 | Hu et al. | 428/690 |
| 2004/0067387 A1 * | 4/2004 | Kim et al. | 428/690 |
| 2004/0214035 A1 * | 10/2004 | Ikeda et al. | 428/690 |
| 2005/0040390 A1 | 2/2005 | Pfeiffer et al. | |
| 2005/0064233 A1 | 3/2005 | Matsuura et al. | |
| 2005/0214565 A1 | 9/2005 | Ikeda et al. | |
| 2005/0233165 A1 | 10/2005 | Ido et al. | |
| 2006/0033421 A1 | 2/2006 | Matsuura et al. | |
| 2006/0035109 A1 * | 2/2006 | Arakane et al. | 428/690 |
| 2006/0040131 A1 * | 2/2006 | Klubek et al. | 428/690 |
| 2006/0043858 A1 | 3/2006 | Ikeda et al. | |
| 2006/0063027 A1 | 3/2006 | Vestweber et al. | |
| 2006/0134456 A1 | 6/2006 | Ikeda et al. | |
| 2006/0175958 A1 | 8/2006 | Gerhard et al. | |
| 2006/0220004 A1 | 10/2006 | Stossel et al. | |
| 2006/0269782 A1 * | 11/2006 | Liao et al. | 428/690 |
| 2007/0055085 A1 * | 3/2007 | Kubota et al. | 585/26 |
| 2007/0134512 A1 * | 6/2007 | Klubek et al. | 428/690 |
| 2007/0164273 A1 | 7/2007 | Gerhard et al. | |
| 2007/0170419 A1 | 7/2007 | Gerhard et al. | |
| 2007/0200490 A1 | 8/2007 | Kawamura et al. | |
| 2008/0125609 A1 | 5/2008 | Vestweber et al. | |

(Continued)

FOREIGN PATENT DOCUMENTS

| | | |
|---|---|---|
| CN | 1362464 A | 8/2002 |
| CN | 1556803 A | 12/2004 |

(Continued)

*Primary Examiner* — Dawn L. Garrett

(74) *Attorney, Agent, or Firm* — Drinker Biddle & Reath LLP

(57) ABSTRACT

The present invention relates to anthracene derivatives, to the use thereof in organic electroluminescent devices, and to organic electroluminescent devices comprising these compounds.

14 Claims, No Drawings

(56) References Cited

U.S. PATENT DOCUMENTS

| | | |
|---|---|---|
| 2008/0145698 A1 | 6/2008 | Heil et al. |
| 2008/0182129 A1 * | 7/2008 | Klubek et al. ................ 428/704 |

FOREIGN PATENT DOCUMENTS

| | | |
|---|---|---|
| EP | 0676461 A2 | 10/1995 |
| EP | 1596445 A1 | 11/2005 |
| EP | 1734038 A1 | 12/2006 |
| JP | 2005515233 A | 5/2005 |
| JP | 2005531552 A | 10/2005 |
| KR | 20040028954 A | 4/2004 |
| WO | WO-98/27136 A1 | 6/1998 |
| WO | WO-01/21729 A1 | 3/2001 |
| WO | WO-01/76323 A1 | 10/2001 |
| WO | WO-03/060956 A2 | 7/2003 |
| WO | WO-03/070822 A2 | 8/2003 |
| WO | WO-03/087023 A1 | 10/2003 |
| WO | WO-03/095445 A1 | 11/2003 |
| WO | WO-2004/013073 A1 | 2/2004 |
| WO | WO-2004/016575 A1 | 2/2004 |
| WO | WO-2004/018587 A1 | 3/2004 |
| WO | WO-2004/018588 A1 | 3/2004 |
| WO | WO-2004/058911 A2 | 7/2004 |
| WO | WO-2004/081017 A1 | 9/2004 |
| WO | WO-2005/011013 A1 | 2/2005 |
| WO | WO-2005054162 A1 | 6/2005 |
| WO | WO-2005/084081 A1 | 9/2005 |
| WO | WO-2005/084082 A1 | 9/2005 |
| WO | WO-2005/097756 A1 | 10/2005 |
| WO | WO-2005097756 A1 | 10/2005 |
| WO | WO-2006/000388 A1 | 1/2006 |
| WO | WO-2006/000389 A1 | 1/2006 |
| WO | WO-2006/048268 A1 | 5/2006 |
| WO | WO-2006/058737 A1 | 6/2006 |
| WO | WO-2006/117052 A1 | 11/2006 |

* cited by examiner

MATERIALS FOR ORGANIC ELECTROLUMINESCENT DEVICES

RELATED APPLICATIONS

This application is a national stage application (under 35 U.S.C. §371) of PCT/EP2007/001732, filed Feb. 28, 2007, which claims benefit of German application 102006013802.3, filed Mar. 24, 2006.

The present invention relates to novel anthracene derivatives, to the use thereof in organic electroluminescent devices, and to organic electroluminescent devices comprising these compounds.

Organic semiconductors are used as functional materials in a number of different applications which can be ascribed to the electronics industry in the broadest sense. The general structure of organic electroluminescent devices which are capable of the emission of light in the visible spectral region is described, for example, in U.S. Pat. No. 4,539,507, U.S. Pat. No. 5,151,629, EP 0676461 and WO 98/27136.

However, these devices still exhibit considerable problems which require urgent improvement for use in high-quality full-colour displays:
1. The efficiency, colour and lifetime of the organic electroluminescent devices are still inadequate for high-quality applications.
2. The compounds used frequently do not have a sufficiently high glass-transition temperature.
3. The redox stability (stability to holes and electrons) of the compounds used to date is still inadequate.
4. The charge-carrier mobility, in particular the electron mobility, is inadequate.
5. The operating voltage should be reduced still further, in particular for mobile applications.

The closest prior art which may be mentioned is the use of various condensed aromatic compounds, in particular anthracene or pyrene derivatives, as host materials, in particular for blue-emitting electroluminescent devices. 9,10-Bis(2-naphthyl)anthracene is known as host material in accordance with the prior art (U.S. Pat. No. 5,935,721). Further anthracene derivatives which are suitable as host materials are described in WO 01/076323, in WO 01/021729, in WO 04/013073, in WO 04/018588, in WO 03/087023 or in WO 04/018587. Host materials based on aryl-substituted pyrenes and chrysenes are described in WO 04/016575. WO 03/095445 and CN 1362464 describe 9,10-bis(1-naphthyl) anthracene derivatives for use in OLEDs.

The object of the present invention was to provide compounds having improved properties, in particular improved host materials.

Surprisingly, it has been found that organic electroluminescent devices which comprise anthracene derivatives which are substituted in the 9,10-position by ortho-substituted phenyl groups and which are furthermore substituted in the 2,6-position by aryl or heteroaryl groups have significant improvements compared with the prior art. The present invention therefore relates to these compounds and to the use thereof in OLEDs.

WO 03/060956 and WO 05/097756 disclose anthracene derivatives which are substituted in the 9,10-position by ortho-biphenyl and which are furthermore substituted in the 2,6-position by aryl groups which contain benzimidazole. The positive effect of these compounds is attributed to the presence of the benzimidazole groups.

The invention relates to compounds of the formula (1)

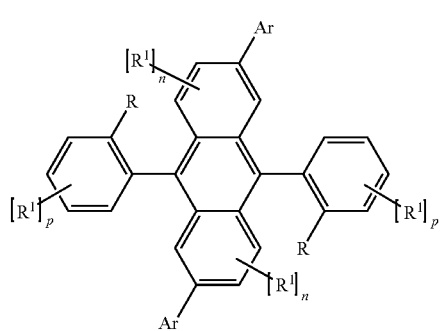

Formula (1)

where the following applies to the symbols and indices used:

Ar is on each occurrence, identically or differently, an aromatic or heteroaromatic ring system having 6 to 30 aromatic ring atoms, which may be substituted by one or more radicals $R^1$;

R, $R^1$ are, identically or differently on each occurrence, F, Cl, Br, I, CN, $N(Ar^1)_2$, $C(=O)Ar^1$, $P(Ar^1)_2$, $P(=O)(Ar^1)_2$, $Si(R^2)_3$, $NO_2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-O-$, $-S-$, $-N(R^2)-$ or $-CONR^2-$ and where one or more H atoms may be replaced by F, Cl, Br, I, CN or $NO_2$, or an aromatic or heteroaromatic ring system having 5 to 30 aromatic ring atoms, which may be substituted by one or more radicals $R^2$ or an aryloxy or heteroaryloxy group having 5 to 24 aromatic ring atoms, which may be substituted by one or more radicals $R^2$, or a combination of two, three, four or five of these systems; adjacent substituents R and $R^1$ or adjacent substituents $R^1$ here may also form a mono- or polycyclic, aliphatic ring system with one another;

$Ar^1$ is on each occurrence, identically or differently, an aromatic or heteroaromatic ring system having 5 to 30 aromatic ring atoms, which may be substituted by one or more non-aromatic radicals $R^1$; two radicals $Ar^1$ here may also be connected to one another by a single bond or an O, S, $N(R^2)$ or $C(R^2)_2$ group;

$R^2$ is on each occurrence, identically or differently, H or a hydrocarbon radical having 1 to 20 C atoms, which may be aliphatic or aromatic or a combination of aliphatic and aromatic and which may also be substituted by F; two or more radicals $R^2$ here may also form a mono- or polycyclic, aliphatic or aromatic ring system with one another;

n is, identically or differently on each occurrence, 0, 1, 2 or 3;

p is, identically or differently on each occurrence, 0, 1, 2, 3 or 4;

with the proviso that the substituents Ar are not substituted or unsubstituted benzimidazole and that no radicals $R^1$ which contain substituted or unsubstituted benzimidazole are bonded to the substituents Ar.

For the purposes of this invention, an aryl group or heteroaryl group is taken to mean an aromatic group or heteroaromatic group respectively having a common aromatic π-electron system. For the purposes of this invention, this may be a simple homo- or heterocycle, for example benzene, pyridine, etc., or it may be a condensed aryl or heteroaryl group in which at least two aromatic or heteroaromatic rings, for example benzene rings, are "fused" to one another, i.e. are condensed onto one another by anellation, i.e. have at least one common edge and thus also a common aromatic π-electron system. These aryl or heteroaryl groups may be substituted or unsubstituted; any substituents present may likewise form further ring systems. Thus, for example, systems such as naphthalene, anthracene, phenanthrene, pyrene, etc., are to be regarded as acyl groups and quinoline, acridine, benzothiophene, carbazole, etc., are as heteroaryl groups for the purposes of this invention, while, for example, biphenyl, fluorene, spirobifluorene, etc., are not aryl groups since they involve separate aromatic electron systems.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the total number of C atoms and heteroatoms is at least 5. The heteroatoms are preferably selected from N, O and/or S. These aromatic and heteroaromatic ring systems may be substituted or unsubstituted; any substituents present may likewise form further ring systems. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an sp$^3$-hybridised C, N or O atom. Thus, for example, systems such as 9,9'-spirobifluorene, fluorene, 9,9-diarylfluorene, triarylamine, diaryl ethers, etc., are also to be regarded as aromatic ring systems for the purposes of this invention. Part of the aromatic or heteroaromatic ring system here may also be a condensed group.

For the purposes of this invention, a cyclic alkyl group is taken to mean both monocyclic and bi- and polycyclic alkyl groups.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoro-methoxy, ethoxy, n-propoxy, i-propoxy, n-butoxy, i-butoxy, s-butoxy, t-butoxy or 2-methylbutoxy. An aromatic or heteroaromatic ring system having 1 to 30 aromatic ring atoms, which may in each case also be substituted by the above-mentioned radicals $R^1$ and $R^2$ and which may be linked to the aromatic or heteroaromatic via any desired positions, is taken to mean, in particular, groups derived from benzene, naphthalene, anthracene, phenanthrene, pyrene, chrysene, perylene, fluoranthene, tetracene, pentacene, benzopyrene, biphenyl, biphenylene, terphenyl, terphenylene, fluorene, spirobifluorene, truxene, isotruxene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole, triphenylamine, diphenylnaphthylamine, dinaphthylphenylamine, diphenyl ether, stilbene and tolan.

Preferred embodiments of compounds of the formula (1) are described below.

Preference is given to compounds of the formula (1) in which the symbol Ar stands for an aryl or heteroaryl group having 6 to 16 aromatic ring atoms, which may be substituted by $R^1$. The symbol Ar particularly preferably stands for phenyl, 2-pyridyl, 3-pyridyl, 4-pyridyl, 1-naphthyl, 2-naphthyl, 2-anthryl, 9-anthryl, 2-phenanthrenyl, 3-phenanthrenyl, 9-phenanthrenyl, 1-pyrenyl or 2-pyrenyl. The symbol Ar very particularly preferably stands for phenyl, 1-naphthyl, 2-naphthyl or 9-anthryl.

Both compounds of the formula (1) in which the two substituents Ar are selected identically and also compounds of the formula (1) in which the substituents Ar are different are in accordance with the invention. In a preferred embodiment of the invention, the two symbols Ar are selected identically. Particular preference is therefore given to the compounds of the formulae (2), (3), (4) and (5)

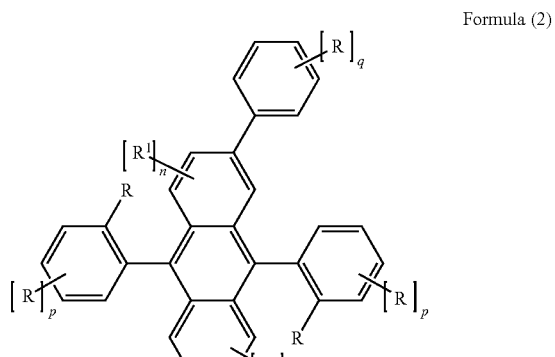

Formula (2)

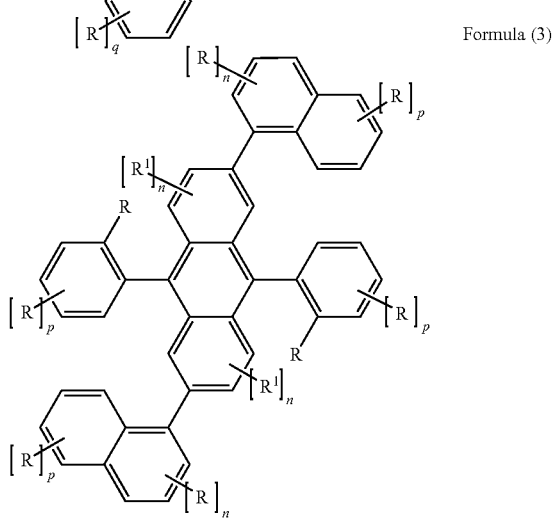

Formula (3)

-continued

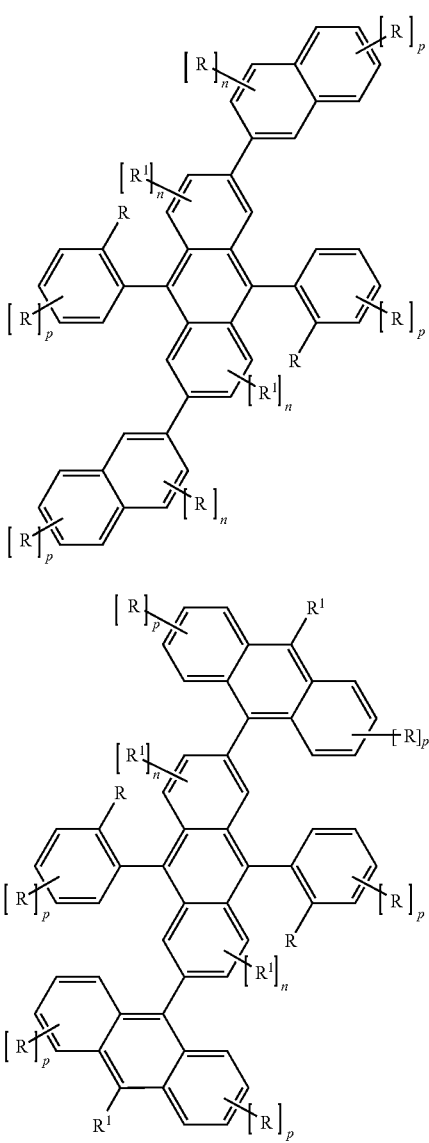

Formula (4)

Formula (5)

in which R, R¹, n and p have the same meaning as described above, and q stands for 0, 1, 2, 3, 4 or 5

In the compounds of the formulae (1) and (2) to (5), the phenyl groups in the 9- and 10-position on the anthracene may have hindered rotation about the anthracene-phenyl bond. For the purposes of this invention, hindered rotation is taken to mean a rotation barrier of at least 80 kJ/mol preferably at least 100 kJ/mol, in particular at least 120 kJ/mol at room temperature. This rotation barrier can be determined experimentally by temperature-dependent NMR measurements. If the compound of the formulae (1) and (2) to (5) exhibits atropisomerism about one or more bonds, the corresponding isolated or enriched atropisomers are in each case also a subject-matter of the invention. This relates both to enantiomers and also to diastereomers. Hindered rotation about the anthracene-phenyl bond is achieved by sufficiently large substituents R.

Preference is furthermore given to compounds of the formulae (1) and (2) to (5) in which the symbol R stands for $Si(R^2)_3$, $N(Ar^1)_2$, $C(=O)Ar^1$, $P(=O)(Ar^1)_2$, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by —$R^2C=CR^2$— or —O— and where one or more H atoms may be replaced by F, or for an aryl or heteroaryl group having 5 to 16 aromatic ring atoms, which may be substituted by one or more radicals $R^2$, or a combination of two, three or four of these systems; adjacent substituents R and R¹ here may also form a mono- or polycyclic, aliphatic ring system with one another. R particularly preferably stands for $Si(R^2)_3$, a straight-chain alkyl group having 1 to 4 C atoms or a branched alkyl group having 3 to 5 C atoms, each of which may be substituted by one or more radicals $R^2$, where one or more H atoms may be replaced by F, or for an aryl or heteroaryl group having 6 to 14 aromatic ring atoms, which may be substituted by one or more radicals $R^2$, or a combination of two or three of these systems; adjacent substituents R and R¹ here may also form a mono- or polycyclic, aliphatic ring system with one another.

Both compounds of the formulae (1) and (2) to (5) in which the two substituents R are selected identically and also compounds of the formulae (1) and (2) to (5) in which the two substituents R are different are in accordance with the invention. The two substituents R are preferably selected identically.

Preference is furthermore given to compounds of the formulae (1) and (2) to (5) in which the symbol R¹, identically or differently on each occurrence, stands for $Si(R^2)_3$, F, $N(Ar^1)_2$, a straight-chain alkyl or alkoxy group having 1 to 6 C atoms or a branched or cyclic alkyl or alkoxy group having 3 to 10 C atoms, where in each case one or more $CH_2$ groups may be replaced by —$R^2C=CR^2$— or —O— and where in each case one or more H atoms may be replaced by F, or an aryl or heteroaryl group having 5 to 14 aromatic ring atoms, which may be substituted by one or more radicals $R^2$, or a combination of two or three of these systems; two or more radicals R¹ here may also form a mono- or polycyclic, aliphatic ring system with one another or with an adjacent radical R. Particularly preferred radicals R¹ are selected from the group consisting of $Si(R^2)_3$, F, straight-chain alkyl groups having 1 to 4 C atoms or branched alkyl groups having 3 to 5 C atoms, where in each case one or more H atoms may be replaced by F, or aryl or heteroaryl groups having 6 to 10 aromatic ring atoms, or a combination of two of these systems; two or more adjacent radicals R¹ here may also form a mono- or polycyclic, aliphatic ring system with one another or with an adjacent radical R.

If one of the radicals R and/or R¹ stands for a group of the formula $N(Ar^1)_2$, it preferably stands for a group of the formula (6) or (7)

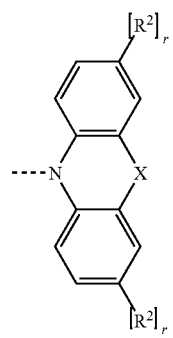

Formula (6)

-continued

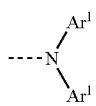
Formula (7)

where R² has the above-mentioned meaning and furthermore:
X stands for a single bond, O, S, N(R²) or C(R²)₂;
Ar¹ is, identically or differently on each occurrence, an aryl or heteroaryl group having 5 to 20 aromatic ring atoms or a triarylamine group having 15 to 30 aromatic ring atoms, each of which may be substituted by one or more radicals R¹, preferably an aryl or heteroaryl group having 6 to 14 aromatic ring atoms or a triarylamine group having 18 to 26 aromatic ring atoms, each of which may be substituted by one or more non-aromatic radicals R¹, particularly preferably phenyl, o-tolyl, p-tolyl, o-fluorophenyl, p-fluorophenyl, 1-naphthyl, 2-naphthyl, triphenylamine or naphthyldiphenylamine;

r is on each occurrence, identically or differently, 0 or 1, preferably 0.

Preference is furthermore given to compounds of the formulae (1) and (2) to (5) in which the index n stands for 0 or 1, particularly preferably for 0.

Preference is furthermore given to compounds of the formulae (1) and (2) to (5) in which the index p stands for 0, 1 or 2, particularly preferably for 0 or 1.

Preference is furthermore given to compounds of the formula (2) in which the index q stands for 0, 1, 2 or 3, particularly preferably for 0, 1 or 2, very particularly preferably for 0 or 1.

Preference is furthermore given to compounds of the formula (1) whose molecular weight is between 500 and 2000 g/mol, particularly preferably between 600 and 1500 g/mol.

Examples of preferred compounds of the formula (1) are compounds (1) to (50) depicted below.

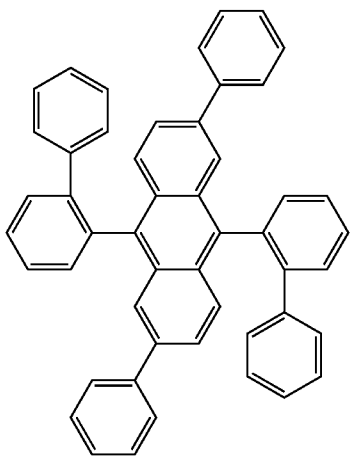
(1)

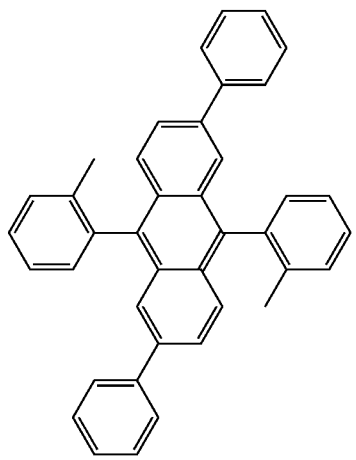
(2)

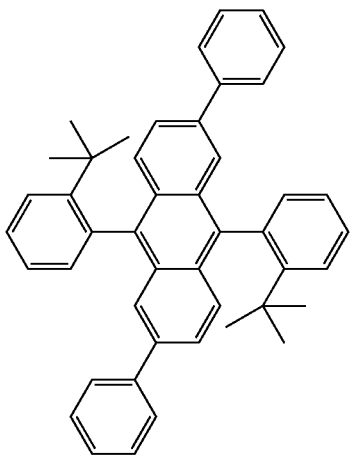
(3)

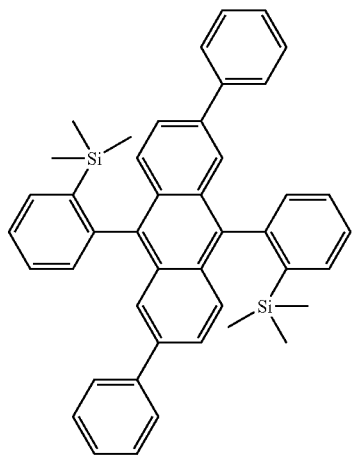
(4)

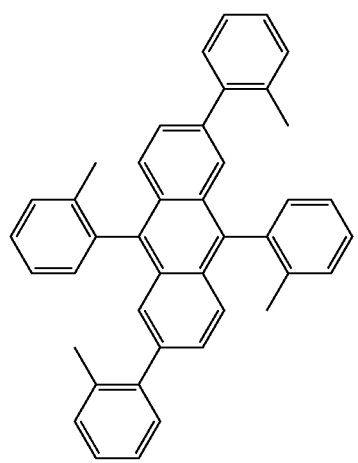
(5)
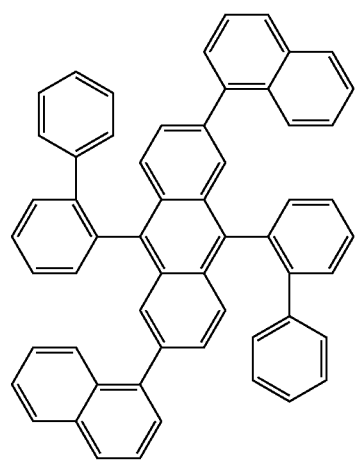
(6)
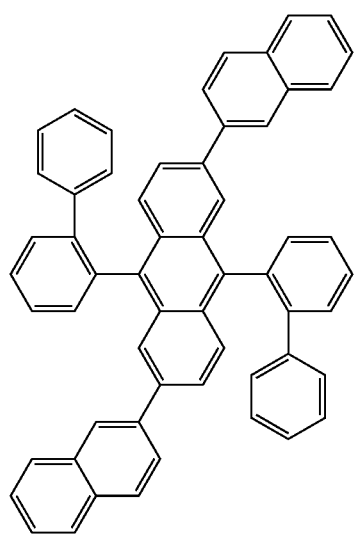
(7)
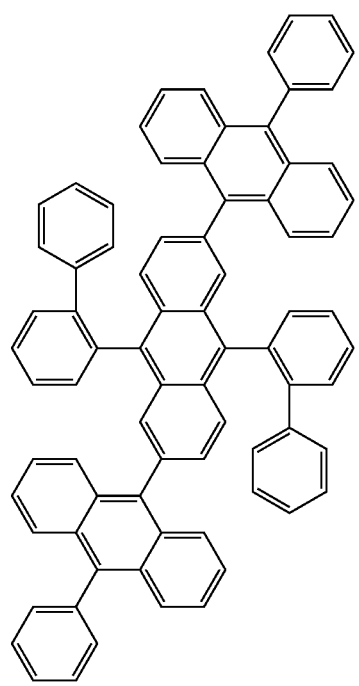
(8)

-continued
(9)
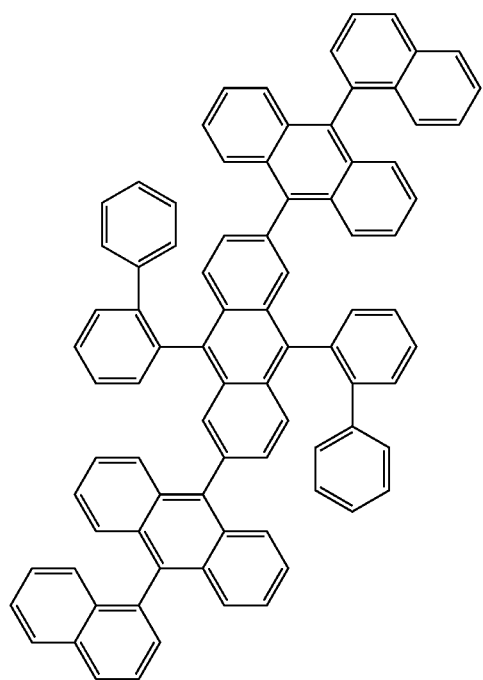
(10)
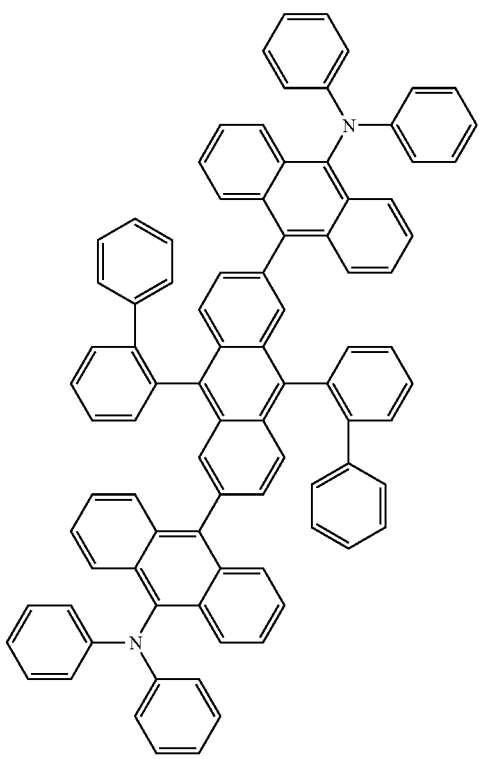
(11)
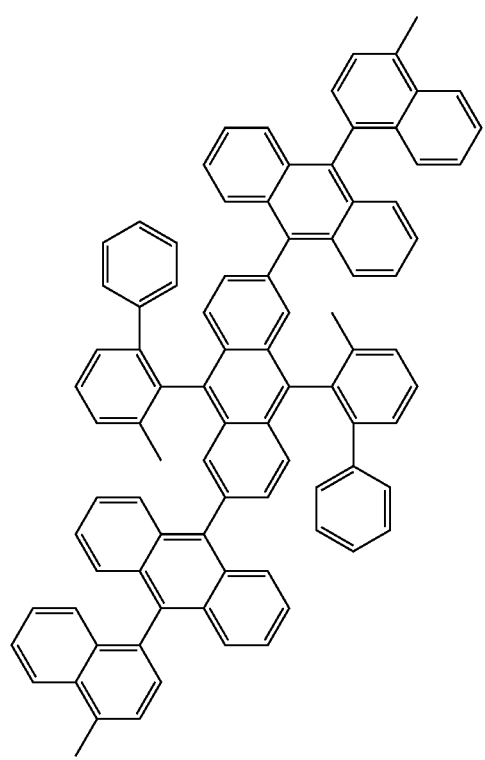
(12)
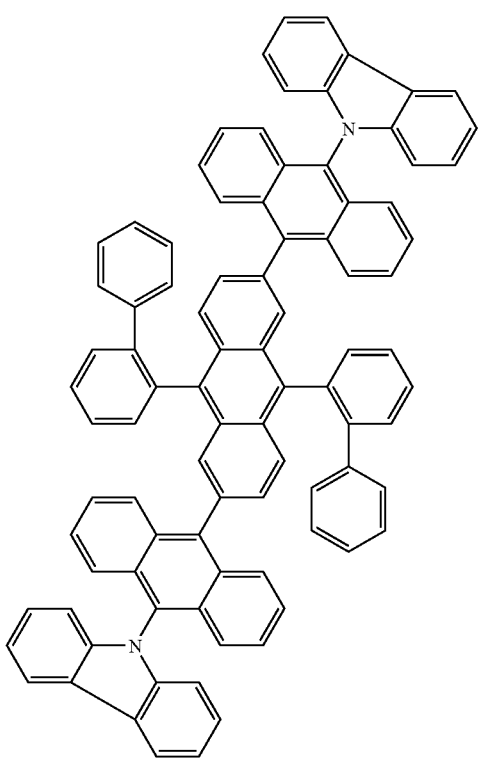

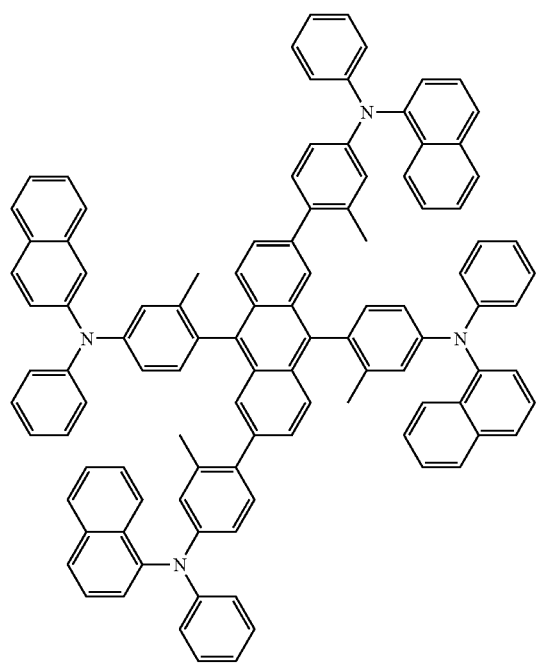
(13)
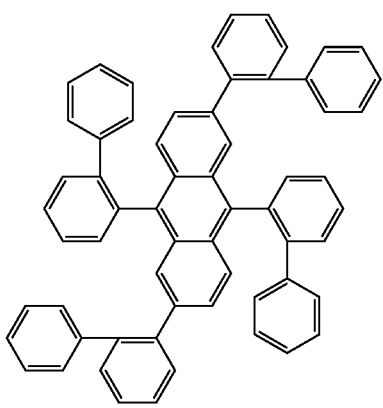
(14)
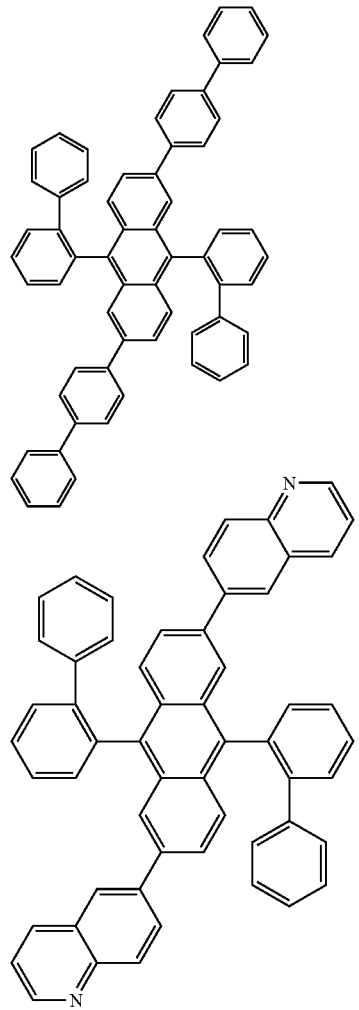
(15)
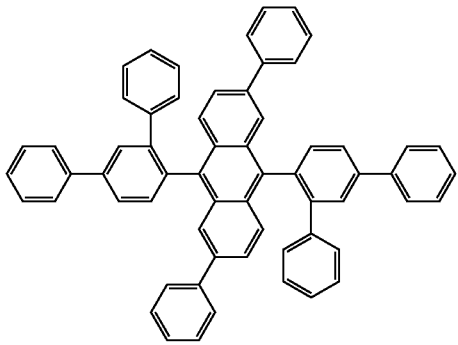
(16)
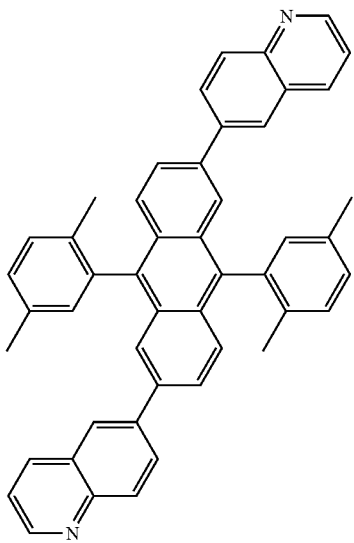
(18)

(19)
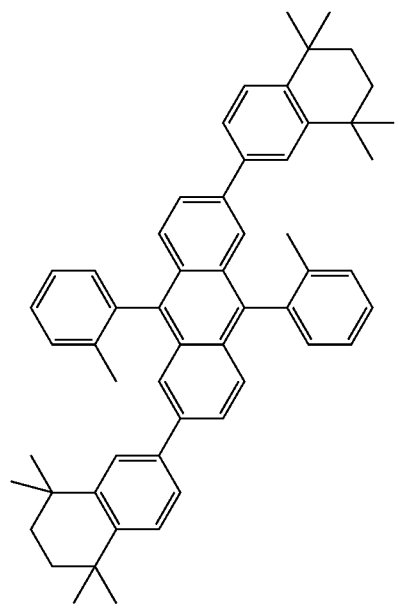
(20)
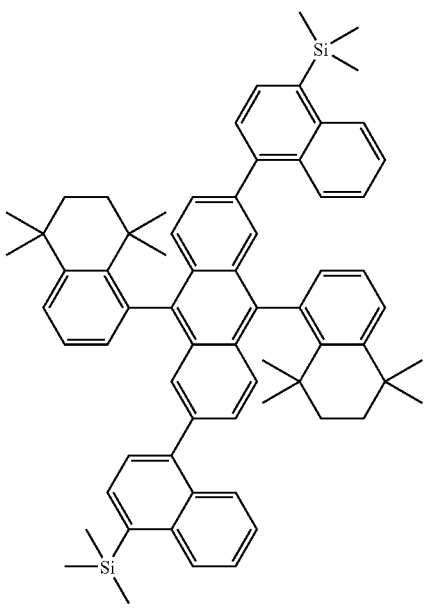
(21)
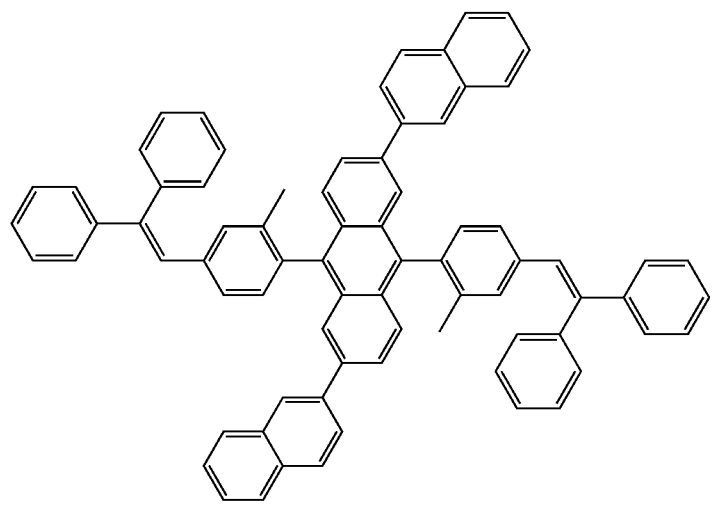
(22)
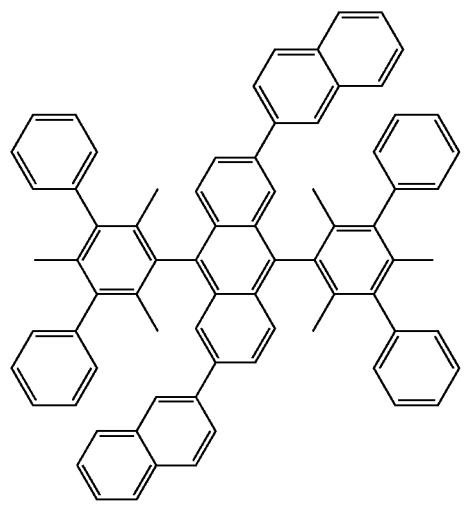
(23)
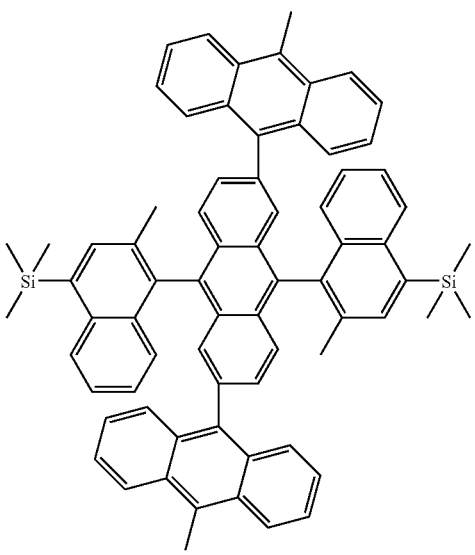

-continued
(24)
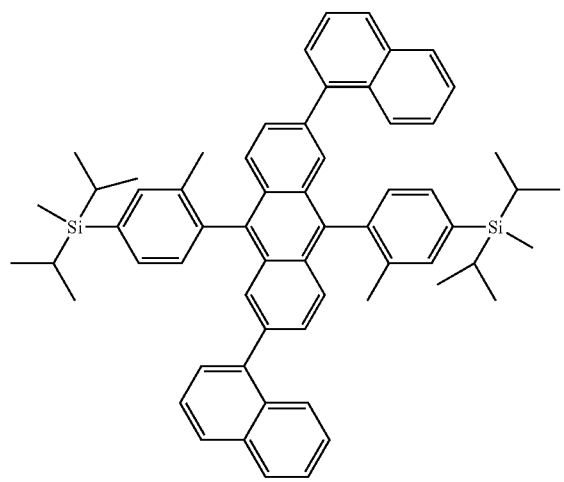
(25)
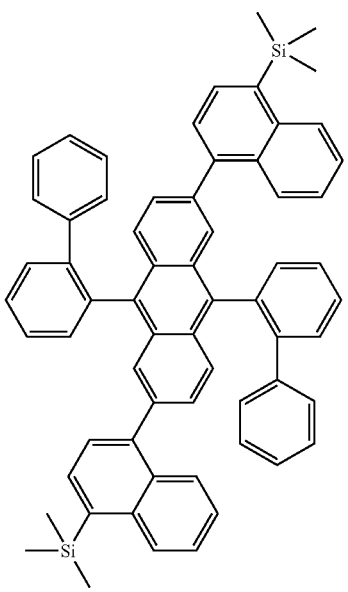
(26)
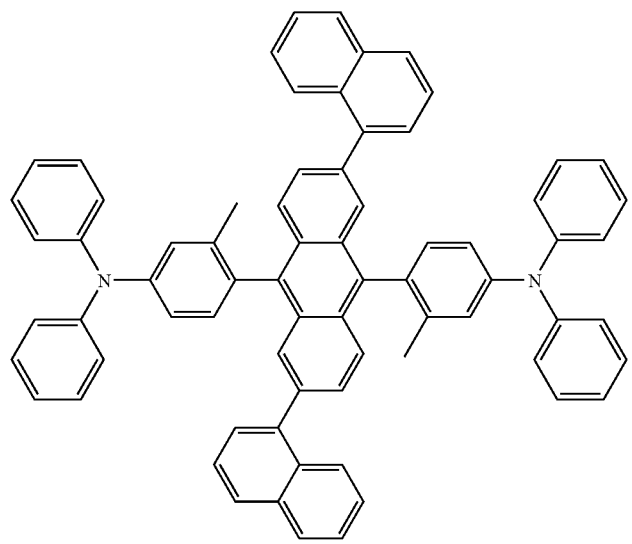

(27)
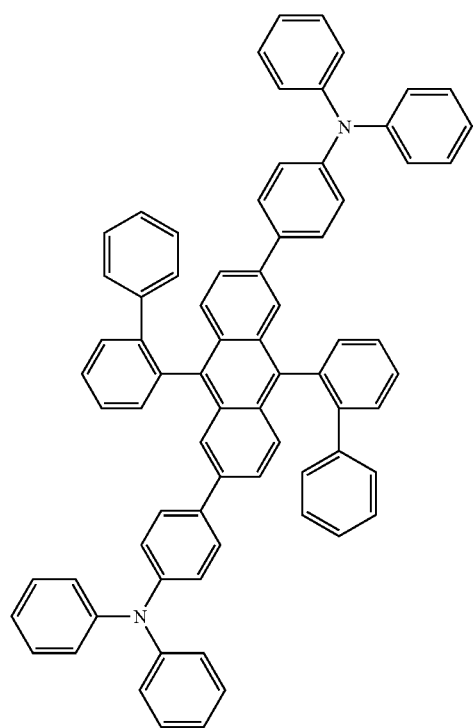
(28)
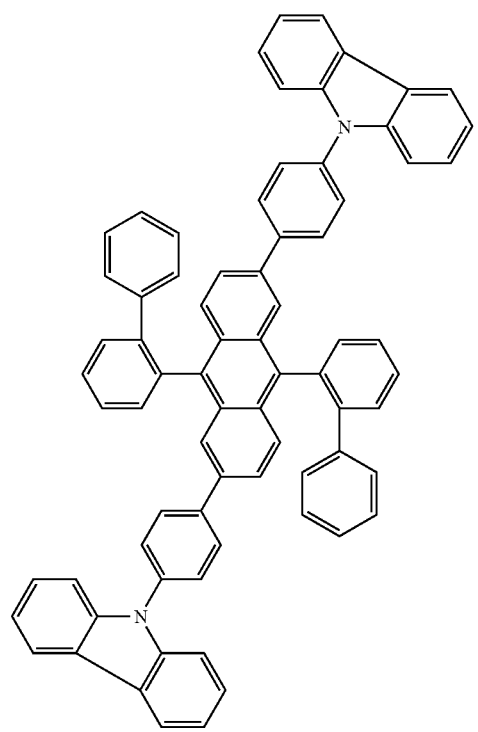
(29)
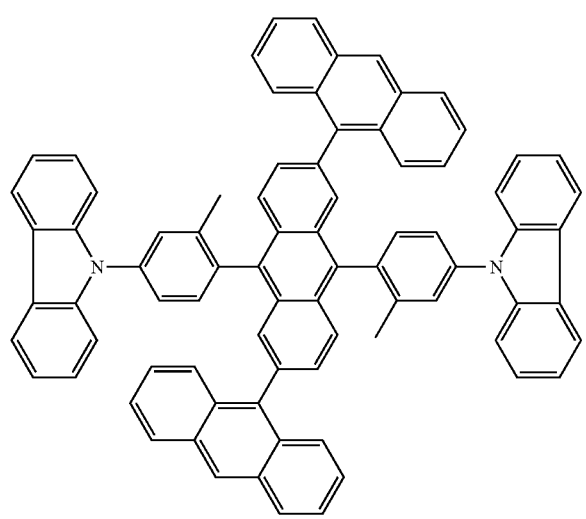
(30)
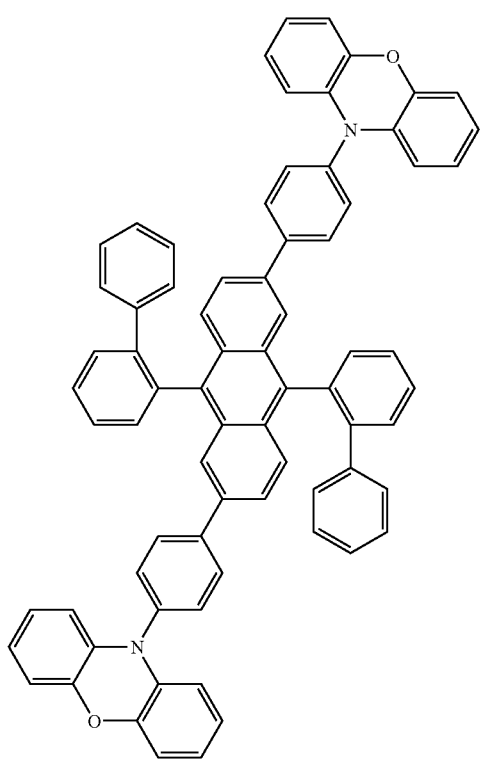

(31)
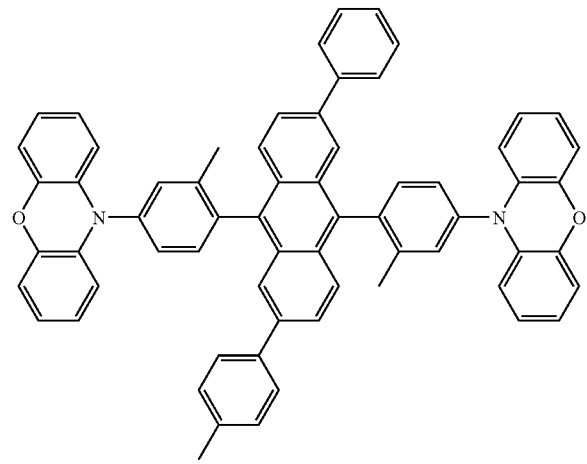
(32)
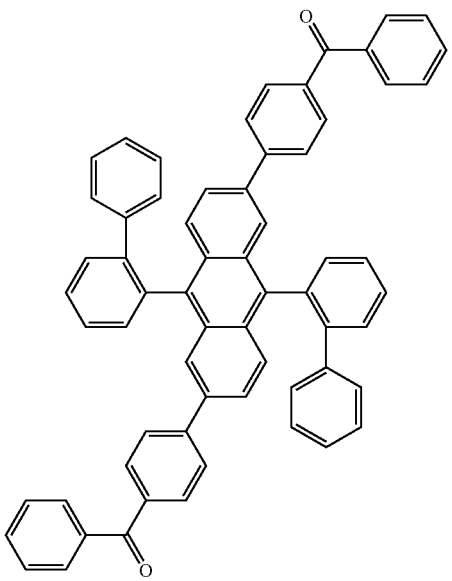
(33)
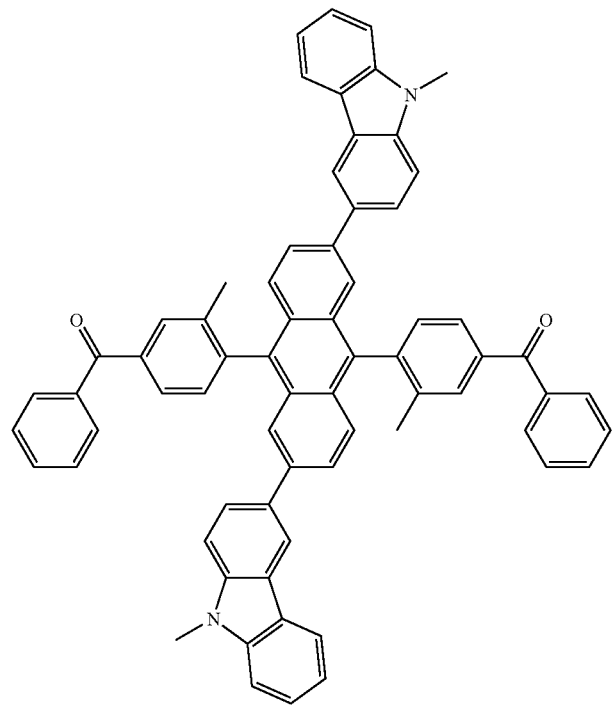

(34)
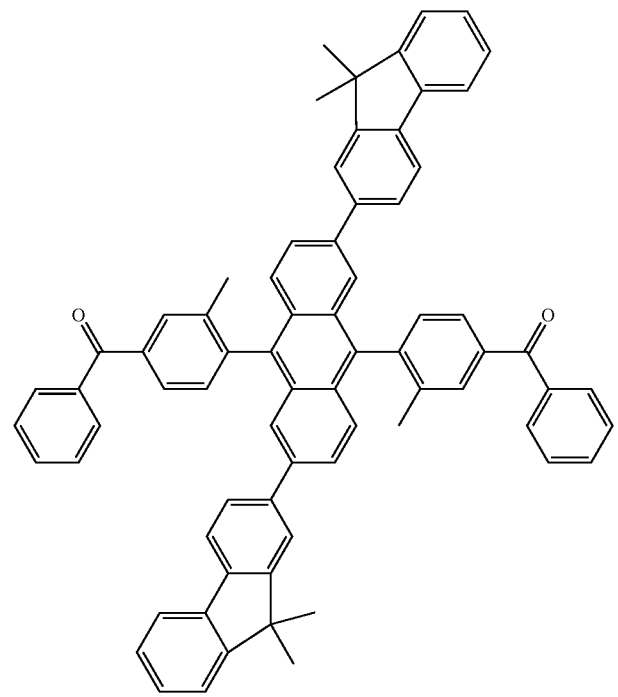
(35)
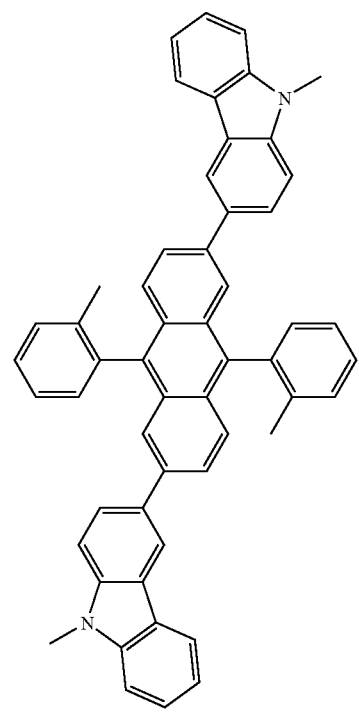
(36)
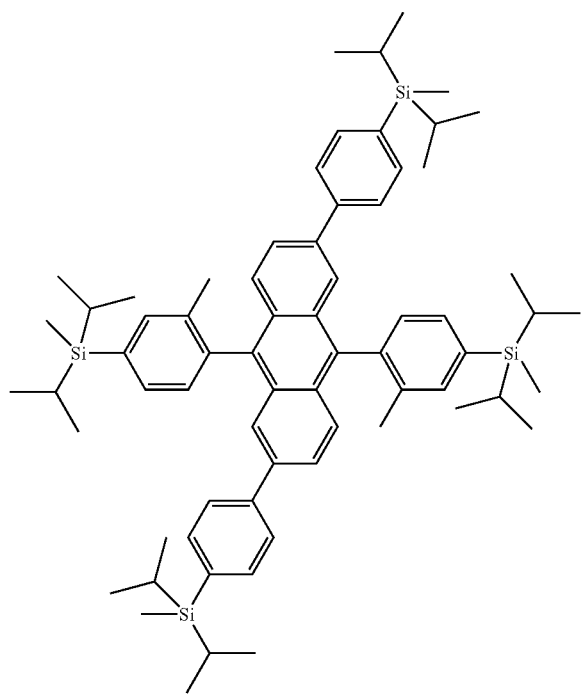

(37)
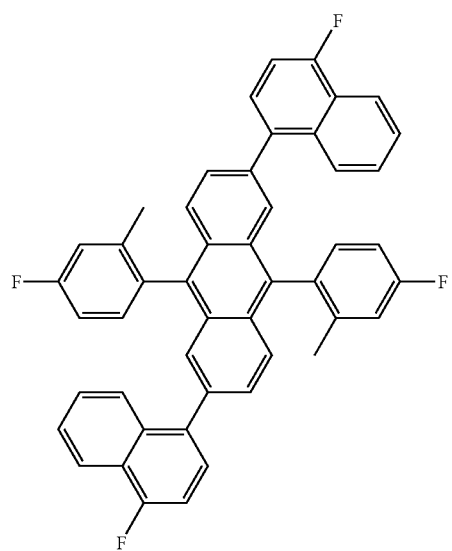
(38)
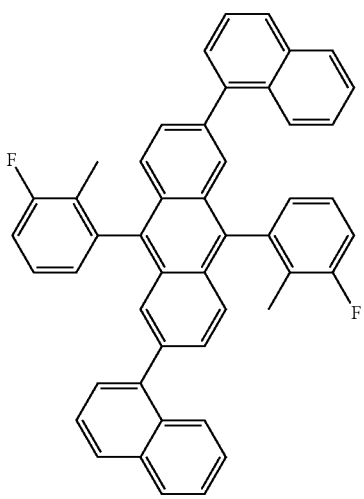
(39)
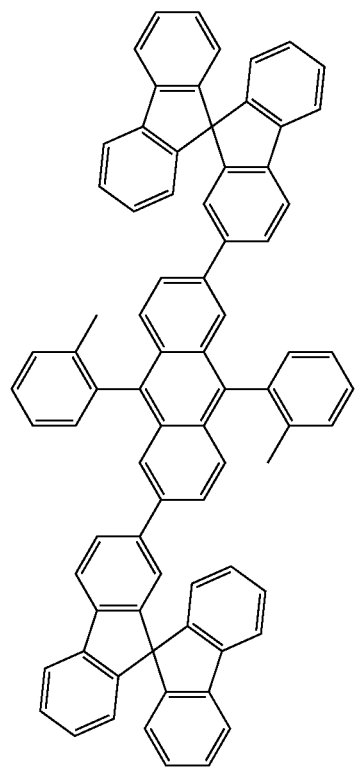
(40)
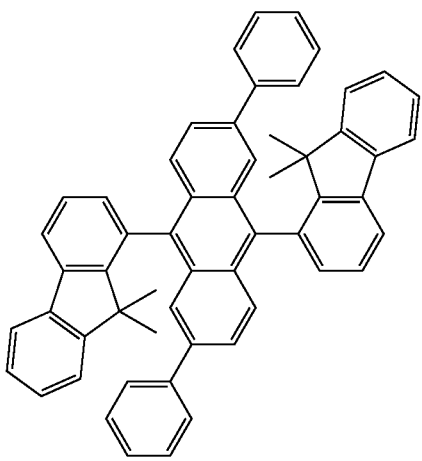

(41)
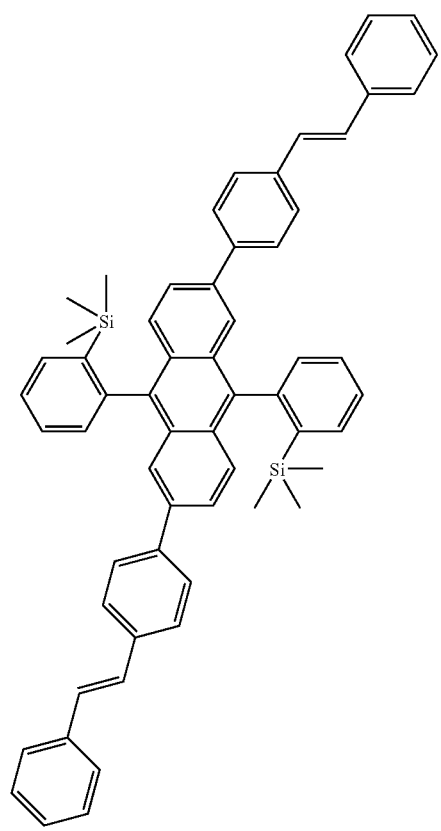
(42)
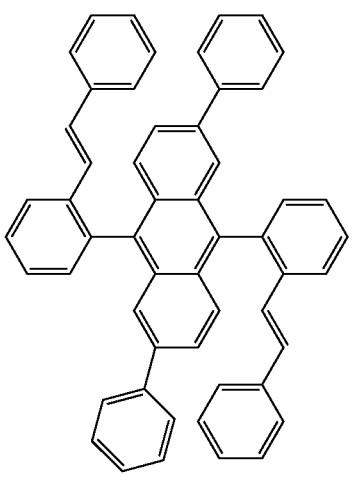
(43)
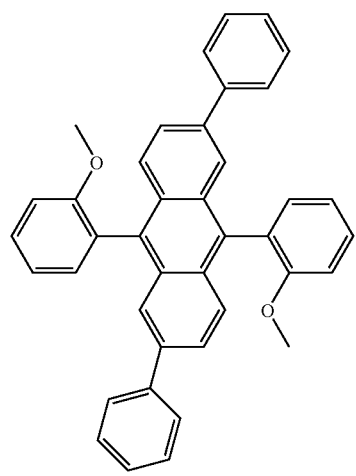
(44)
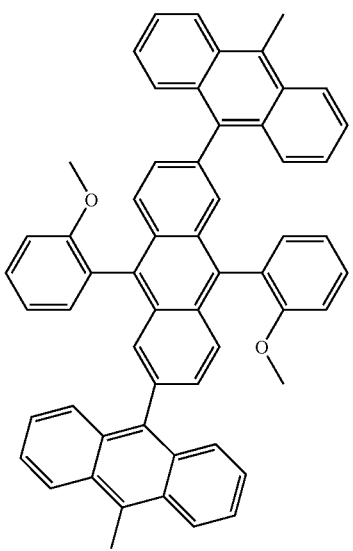

-continued
(45)
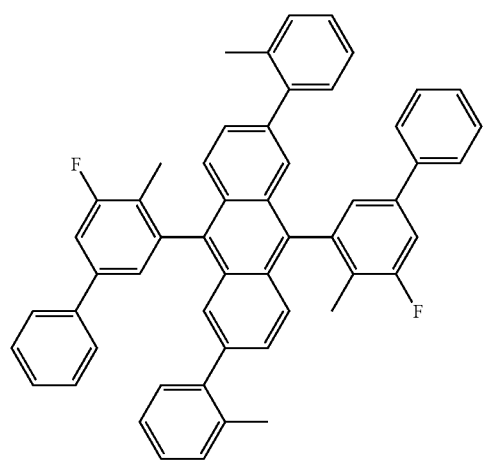
(46)
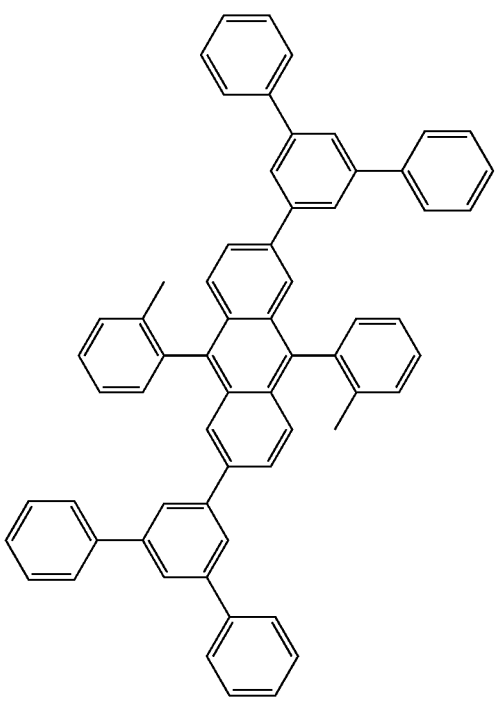
(47)
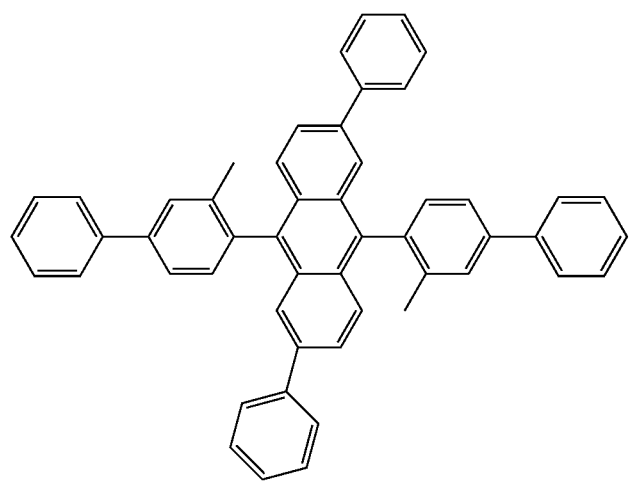

-continued
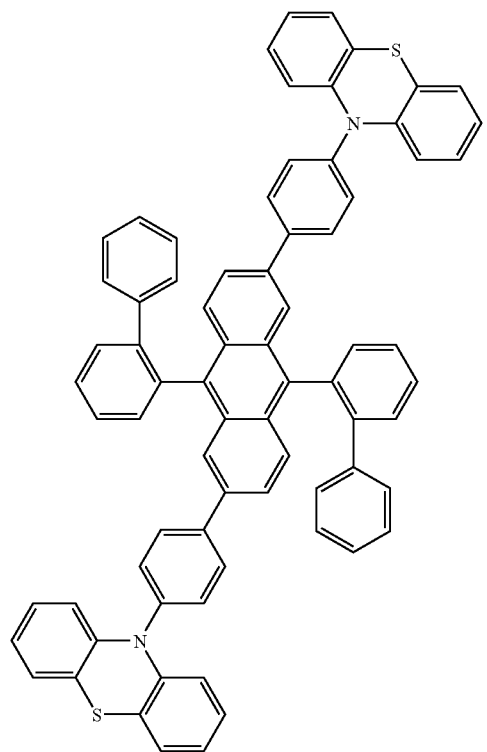
(48)
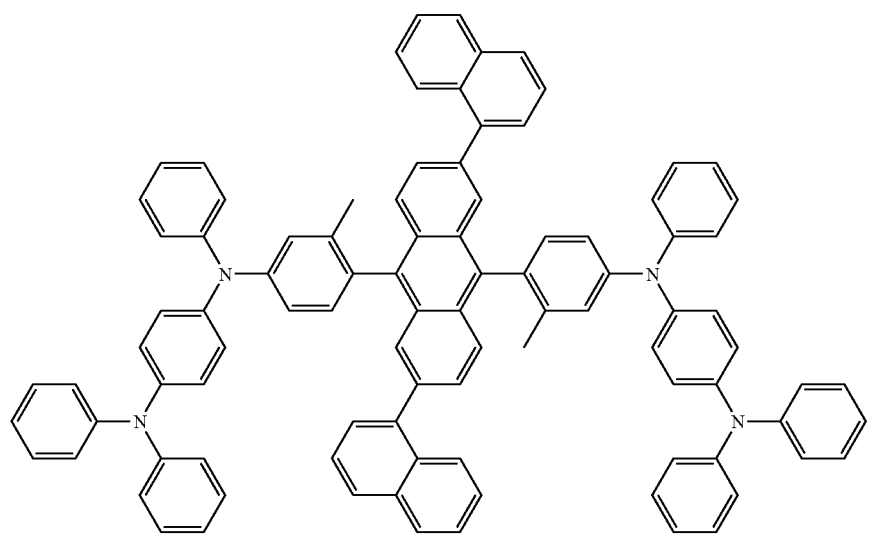
(49)

(50)
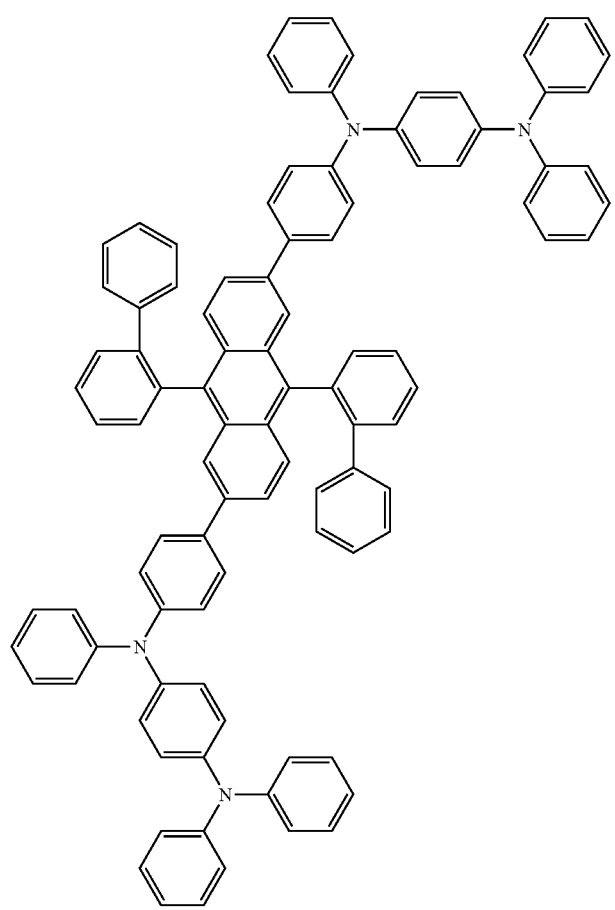
Table 1 below indicates further preferred structures of the formula (1). The symbols and indices used in the table relate to formula (8) depicted below:
Formula (8)
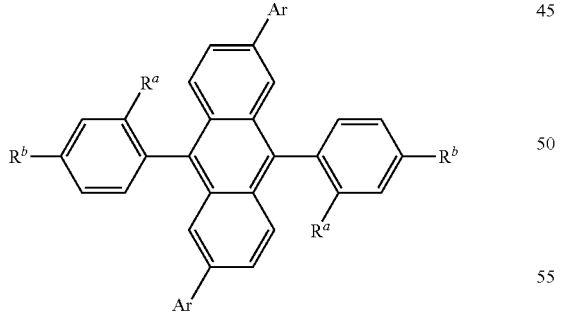
Ar here stands for a group of the formula (9), (10) or (11):
Formula (9)
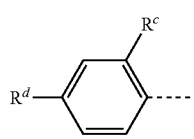
Formula (10)
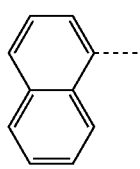
Formula (11)
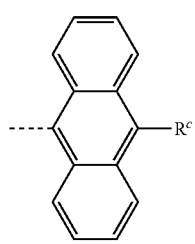
where the dashed bond denotes the link to the anthracene unit.

Furthermore, the abbreviation N(p-Tol)$_2$ in Table 1 stands for a bis(para-tolyl)amino group.

TABLE 1

Preferred structures of the formula (8)

| No. | Ar | Rc | Rd | Ra | Rb |
|---|---|---|---|---|---|
| 1 | Phenyl | H | H | Methyl | H |
| 2 | Phenyl | H | H | Methyl | Methyl |
| 3 | Phenyl | H | H | Methyl | tert-Butyl |
| 4 | Phenyl | H | H | Methyl | Si(Me)$_3$ |
| 5 | Phenyl | H | H | Methyl | N(p-Tol)$_2$ |
| 6 | Phenyl | H | H | Methyl | Phenyl |
| 7 | Phenyl | H | H | tert-Butyl | H |
| 8 | Phenyl | H | H | tert-Butyl | Methyl |
| 9 | Phenyl | H | H | tert-Butyl | tert-Butyl |
| 10 | Phenyl | H | H | tert-Butyl | Si(Me)$_3$ |
| 11 | Phenyl | H | H | tert-Butyl | N(p-Tol)$_2$ |
| 12 | Phenyl | H | H | tert-Butyl | Phenyl |
| 13 | Phenyl | H | H | Si(Me)$_3$ | H |
| 14 | Phenyl | H | H | Si(Me)$_3$ | Methyl |
| 15 | Phenyl | H | H | Si(Me)$_3$ | tert-Butyl |
| 16 | Phenyl | H | H | Si(Me)$_3$ | Si(Me)$_3$ |
| 17 | Phenyl | H | H | Si(Me)$_3$ | N(p-Tol)$_2$ |
| 18 | Phenyl | H | H | Si(Me)$_3$ | Phenyl |
| 19 | Phenyl | H | H | N(p-Tol)$_2$ | H |
| 20 | Phenyl | H | H | N(p-Tol)$_2$ | Methyl |
| 21 | Phenyl | H | H | N(p-Tol)$_2$ | tert-Butyl |
| 22 | Phenyl | H | H | N(p-Tol)$_2$ | Si(Me)$_3$ |
| 23 | Phenyl | H | H | N(p-Tol)$_2$ | N(p-Tol)$_2$ |
| 24 | Phenyl | H | H | N(p-Tol)$_2$ | Phenyl |
| 25 | Phenyl | H | H | Phenyl | H |
| 26 | Phenyl | H | H | Phenyl | Methyl |
| 27 | Phenyl | H | H | Phenyl | tert-Butyl |
| 28 | Phenyl | H | H | Phenyl | Si(Me)$_3$ |
| 29 | Phenyl | H | H | Phenyl | N(p-Tol)$_2$ |
| 30 | Phenyl | H | H | Phenyl | Phenyl |
| 31 | Phenyl | H | Methyl | Methyl | H |
| 32 | Phenyl | H | Methyl | Methyl | Methyl |
| 33 | Phenyl | H | Methyl | Methyl | tert-Butyl |
| 34 | Phenyl | H | Methyl | Methyl | Si(Me)$_3$ |
| 35 | Phenyl | H | Methyl | Methyl | N(p-Tol)$_2$ |
| 36 | Phenyl | H | Methyl | Methyl | Phenyl |
| 37 | Phenyl | H | Methyl | tert-Butyl | H |
| 38 | Phenyl | H | Methyl | tert-Butyl | Methyl |
| 39 | Phenyl | H | Methyl | tert-Butyl | tert-Butyl |
| 40 | Phenyl | H | Methyl | tert-Butyl | Si(Me)$_3$ |
| 41 | Phenyl | H | Methyl | tert-Butyl | N(p-Tol)$_2$ |
| 42 | Phenyl | H | Methyl | tert-Butyl | Phenyl |
| 43 | Phenyl | H | Methyl | Si(Me)$_3$ | H |
| 44 | Phenyl | H | Methyl | Si(Me)$_3$ | Methyl |
| 45 | Phenyl | H | Methyl | Si(Me)$_3$ | tert-Butyl |
| 46 | Phenyl | H | Methyl | Si(Me)$_3$ | Si(Me)$_3$ |
| 47 | Phenyl | H | Methyl | Si(Me)$_3$ | N(p-Tol)$_2$ |
| 48 | Phenyl | H | Methyl | Si(Me)$_3$ | Phenyl |
| 49 | Phenyl | H | Methyl | N(p-Tol)$_2$ | H |
| 50 | Phenyl | H | Methyl | N(p-Tol)$_2$ | Methyl |
| 51 | Phenyl | H | Methyl | N(p-Tol)$_2$ | tert-Butyl |
| 52 | Phenyl | H | Methyl | N(p-Tol)$_2$ | Si(Me)$_3$ |
| 53 | Phenyl | H | Methyl | N(p-Tol)$_2$ | N(p-Tol)$_2$ |
| 54 | Phenyl | H | Methyl | N(p-Tol)$_2$ | Phenyl |
| 55 | Phenyl | H | Methyl | Phenyl | H |
| 56 | Phenyl | H | Methyl | Phenyl | Methyl |
| 57 | Phenyl | H | Methyl | Phenyl | tert-Butyl |
| 58 | Phenyl | H | Methyl | Phenyl | Si(Me)$_3$ |
| 59 | Phenyl | H | Methyl | Phenyl | N(p-Tol)$_2$ |
| 60 | Phenyl | H | Methyl | Phenyl | Phenyl |
| 61 | Phenyl | H | tert-Butyl | Methyl | H |
| 62 | Phenyl | H | tert-Butyl | Methyl | Methyl |
| 63 | Phenyl | H | tert-Butyl | Methyl | tert-Butyl |
| 64 | Phenyl | H | tert-Butyl | Methyl | Si(Me)3 |
| 65 | Phenyl | H | tert-Butyl | Methyl | N(p-Tol)$_2$ |
| 66 | Phenyl | H | tert-Butyl | Methyl | Phenyl |
| 67 | Phenyl | H | tert-Butyl | tert-Butyl | H |
| 68 | Phenyl | H | tert-Butyl | tert-Butyl | Methyl |
| 69 | Phenyl | H | tert-Butyl | tert-Butyl | tert-Butyl |
| 70 | Phenyl | H | tert-Butyl | tert-Butyl | Si(Me)$_3$ |
| 71 | Phenyl | H | tert-Butyl | tert-Butyl | N(p-Tol)$_2$ |
| 72 | Phenyl | H | tert-Butyl | tert-Butyl | Phenyl |
| 73 | Phenyl | H | tert-Butyl | Si(Me)$_3$ | H |
| 74 | Phenyl | H | tert-Butyl | Si(Me)$_3$ | Methyl |
| 75 | Phenyl | H | tert-Butyl | Si(Me)$_3$ | tert-Butyl |
| 76 | Phenyl | H | tert-Butyl | Si(Me)$_3$ | Si(Me)$_3$ |
| 77 | Phenyl | H | tert-Butyl | Si(Me)$_3$ | N(p-Tol)$_2$ |
| 78 | Phenyl | H | tert-Butyl | Si(Me)$_3$ | Phenyl |
| 79 | Phenyl | H | tert-Butyl | N(p-Tol)$_2$ | H |
| 80 | Phenyl | H | tert-Butyl | N(p-Tol)$_2$ | Methyl |
| 81 | Phenyl | H | tert-Butyl | N(p-Tol)$_2$ | tert-Butyl |
| 82 | Phenyl | H | tert-Butyl | N(p-Tol)$_2$ | Si(Me)$_3$ |
| 83 | Phenyl | H | tert-Butyl | N(p-Tol)$_2$ | N(p-Tol)$_2$ |
| 84 | Phenyl | H | tert-Butyl | N(p-Tol)$_2$ | Phenyl |
| 85 | Phenyl | H | tert-Butyl | Phenyl | H |
| 86 | Phenyl | H | tert-Butyl | Phenyl | Methyl |
| 87 | Phenyl | H | tert-Butyl | Phenyl | tert-Butyl |
| 88 | Phenyl | H | tert-Butyl | Phenyl | Si(Me)$_3$ |
| 89 | Phenyl | H | tert-Butyl | Phenyl | N(p-Tol)$_2$ |
| 90 | Phenyl | H | tert-Butyl | Phenyl | Phenyl |
| 91 | Phenyl | H | Si(Me)$_3$ | Methyl | H |
| 92 | Phenyl | H | Si(Me)$_3$ | Methyl | Methyl |
| 93 | Phenyl | H | Si(Me)$_3$ | Methyl | tert-Butyl |
| 94 | Phenyl | H | Si(Me)$_3$ | Methyl | Si(Me)$_3$ |
| 95 | Phenyl | H | Si(Me)$_3$ | Methyl | N(p-Tol)$_2$ |
| 96 | Phenyl | H | Si(Me)$_3$ | Methyl | Phenyl |
| 97 | Phenyl | H | Si(Me)$_3$ | tert-Butyl | H |
| 98 | Phenyl | H | Si(Me)$_3$ | tert-Butyl | Methyl |
| 99 | Phenyl | H | Si(Me)$_3$ | tert-Butyl | tert-Butyl |
| 100 | Phenyl | H | Si(Me)$_3$ | tert-Butyl | Si(Me)$_3$ |
| 101 | Phenyl | H | Si(Me)$_3$ | tert-Butyl | N(p-Tol)$_2$ |
| 102 | Phenyl | H | Si(Me)$_3$ | tert-Butyl | Phenyl |
| 103 | Phenyl | H | Si(Me)$_3$ | Si(Me)$_3$ | H |
| 104 | Phenyl | H | Si(Me)$_3$ | Si(Me)$_3$ | Methyl |
| 105 | Phenyl | H | Si(Me)$_3$ | Si(Me)$_3$ | tert-Butyl |
| 106 | Phenyl | H | Si(Me)$_3$ | Si(Me)$_3$ | Si(Me)$_3$ |
| 107 | Phenyl | H | Si(Me)$_3$ | Si(Me)$_3$ | N(p-Tol)$_2$ |
| 108 | Phenyl | H | Si(Me)$_3$ | Si(Me)$_3$ | Phenyl |
| 109 | Phenyl | H | Si(Me)$_3$ | N(p-Tol)$_2$ | H |
| 110 | Phenyl | H | Si(Me)$_3$ | N(p-Tol)$_2$ | Methyl |
| 111 | Phenyl | H | Si(Me)$_3$ | N(p-Tol)$_2$ | tert-Butyl |
| 112 | Phenyl | H | Si(Me)$_3$ | N(p-Tol)$_2$ | Si(Me)$_3$ |
| 113 | Phenyl | H | Si(Me)$_3$ | N(p-Tol)$_2$ | N(p-Tol)$_2$ |
| 114 | Phenyl | H | Si(Me)$_3$ | N(p-Tol)$_2$ | Phenyl |
| 115 | Phenyl | H | Si(Me)$_3$ | Phenyl | H |
| 116 | Phenyl | H | Si(Me)$_3$ | Phenyl | Methyl |
| 117 | Phenyl | H | Si(Me)$_3$ | Phenyl | tert-Butyl |
| 118 | Phenyl | H | Si(Me)3 | Phenyl | Si(Me)$_3$ |
| 119 | Phenyl | H | Si(Me)$_3$ | Phenyl | N(p-Tol)$_2$ |
| 120 | Phenyl | H | Si(Me)$_3$ | Phenyl | Phenyl |
| 121 | Phenyl | H | N(p-Tol)$_2$ | Methyl | H |
| 122 | Phenyl | H | N(p-Tol)$_2$ | Methyl | Methyl |
| 123 | Phenyl | H | N(p-Tol)$_2$ | Methyl | tert-Butyl |
| 124 | Phenyl | H | N(p-Tol)$_2$ | Methyl | Si(Me)$_3$ |
| 125 | Phenyl | H | N(p-Tol)$_2$ | Methyl | N(p-Tol)$_2$ |
| 126 | Phenyl | H | N(p-Tol)$_2$ | Methyl | Phenyl |
| 127 | Phenyl | H | N(p-Tol)$_2$ | tert-Butyl | H |
| 128 | Phenyl | H | N(p-Tol)$_2$ | tert-Butyl | Methyl |
| 129 | Phenyl | H | N(p-Tol)$_2$ | tert-Butyl | tert-Butyl |
| 130 | Phenyl | H | N(p-Tol)$_2$ | tert-Butyl | Si(Me)$_3$ |
| 131 | Phenyl | H | N(p-Tol)$_2$ | tert-Butyl | N(p-Tol)$_2$ |
| 132 | Phenyl | H | N(p-Tol)$_2$ | tert-Butyl | Phenyl |
| 133 | Phenyl | H | N(p-Tol)$_2$ | Si(Me)$_3$ | H |
| 134 | Phenyl | H | N(p-Tol)$_2$ | Si(Me)$_3$ | Methyl |
| 135 | Phenyl | H | N(p-Tol)$_2$ | Si(Me)$_3$ | tert-Butyl |
| 136 | Phenyl | H | N(p-Tol)$_2$ | Si(Me$\}_3$ | Si(Me)$_3$ |
| 137 | Phenyl | H | N(p-Tol)$_2$ | Si(Me)$_3$ | N(p-Tol)$_2$ |
| 138 | Phenyl | H | N(p-Tol)$_2$ | Si(Me)$_3$ | Phenyl |
| 139 | Phenyl | H | N(p-Tol)$_2$ | N(p-Tol)$_2$ | H |
| 140 | Phenyl | H | N(p-Tol)$_2$ | N(p-Tol)$_2$ | Methyl |
| 141 | Phenyl | H | N(p-Tol)$_2$ | N(p-Tol)$_2$ | tert-Butyl |
| 142 | Phenyl | H | N(p-Tol)$_2$ | N(p-Tol)$_2$ | Si(Me)$_3$ |
| 143 | Phenyl | H | N(p-Tol)$_2$ | N(p-Tol)$_2$ | N(p-Tol)$_2$ |
| 144 | Phenyl | H | N(p-Tol)$_2$ | N(p-Tol)$_2$ | Phenyl |

TABLE 1-continued

Preferred structures of the formula (8)

| No. | Ar | Rc | Rd | Ra | Rb |
|---|---|---|---|---|---|
| 145 | Phenyl | H | N(p-Tol)$_2$ | Phenyl | H |
| 146 | Phenyl | H | N(p-Tol)$_2$ | Phenyl | Methyl |
| 147 | Phenyl | H | N(p-Tol)$_2$ | Phenyl | tert-Butyl |
| 148 | Phenyl | H | N(p-Tol)$_2$ | Phenyl | Si(Me)$_3$ |
| 149 | Phenyl | H | N(p-Tol)$_2$ | Phenyl | N(p-Tol)$_2$ |
| 150 | Phenyl | H | N(p-Tol)$_2$ | Phenyl | Phenyl |
| 151 | Phenyl | Methyl | H | Methyl | H |
| 152 | Phenyl | Methyl | H | Methyl | Methyl |
| 153 | Phenyl | Methyl | H | Methyl | tert-Butyl |
| 154 | Phenyl | Methyl | H | Methyl | Si(Me)$_3$ |
| 155 | Phenyl | Methyl | H | Methyl | N(p-Tol)$_2$ |
| 156 | Phenyl | Methyl | H | Methyl | Phenyl |
| 157 | Phenyl | Methyl | H | tert-Butyl | H |
| 158 | Phenyl | Methyl | H | tert-Butyl | Methyl |
| 159 | Phenyl | Methyl | H | tert-Butyl | tert-Butyl |
| 160 | Phenyl | Methyl | H | tert-Butyl | Si(Me)$_3$ |
| 161 | Phenyl | Methyl | H | tert-Butyl | N(p-Tol)$_2$ |
| 162 | Phenyl | Methyl | H | tert-Butyl | Phenyl |
| 163 | Phenyl | Methyl | H | Si(Me)$_3$ | H |
| 164 | Phenyl | Methyl | H | Si(Me)$_3$ | Methyl |
| 165 | Phenyl | Methyl | H | Si(Me)$_3$ | tert-Butyl |
| 166 | Phenyl | Methyl | H | Si(Me)$_3$ | Si(Me)$_3$ |
| 167 | Phenyl | Methyl | H | Si(Me)$_3$ | N(p-Tol)$_2$ |
| 168 | Phenyl | Methyl | H | Si(Me)$_3$ | Phenyl |
| 169 | Phenyl | Methyl | H | N(p-Tol)$_2$ | H |
| 170 | Phenyl | Methyl | H | N(p-Tol)$_2$ | Methyl |
| 171 | Phenyl | Methyl | H | N(p-Tol)$_2$ | tert-Butyl |
| 172 | Phenyl | Methyl | H | N(p-Tol)$_2$ | Si(Me)$_3$ |
| 173 | Phenyl | Methyl | H | N(p-Tol)$_2$ | N(p-Tol)$_2$ |
| 174 | Phenyl | Methyl | H | N(p-Tol)$_2$ | Phenyl |
| 175 | Phenyl | Methyl | H | Phenyl | H |
| 176 | Phenyl | Methyl | H | Phenyl | Methyl |
| 177 | Phenyl | Methyl | H | Phenyl | tert-Butyl |
| 178 | Phenyl | Methyl | H | Phenyl | Si(Me)$_3$ |
| 179 | Phenyl | Methyl | H | Phenyl | N(p-Tol)$_2$ |
| 180 | Phenyl | Methyl | H | Phenyl | Phenyl |
| 181 | Phenyl | tert-Butyl | H | Methyl | H |
| 182 | Phenyl | tert-Butyl | H | Methyl | Methyl |
| 183 | Phenyl | tert-Butyl | H | Methyl | tert-Butyl |
| 184 | Phenyl | tert-Butyl | H | Methyl | Si(Me)$_3$ |
| 185 | Phenyl | tert-Butyl | H | Methyl | N(p-Tol)$_2$ |
| 186 | Phenyl | tert-Butyl | H | Methyl | Phenyl |
| 187 | Phenyl | tert-Butyl | H | tert-Butyl | H |
| 188 | Phenyl | tert-Butyl | H | tert-Butyl | Methyl |
| 189 | Phenyl | tert-Butyl | H | tert-Butyl | tert-Butyl |
| 190 | Phenyl | tert-Butyl | H | tert-Butyl | Si(Me)$_3$ |
| 191 | Phenyl | tert-Butyl | H | tert-Butyl | N(p-Tol)$_2$ |
| 192 | Phenyl | tert-Butyl | H | tert-Butyl | Phenyl |
| 193 | Phenyl | tert-Butyl | H | Si(Me)$_3$ | H |
| 194 | Phenyl | tert-Butyl | H | Si(Me)$_3$ | Methyl |
| 195 | Phenyl | tert-Butyl | H | Si(Me)$_3$ | tert-Butyl |
| 196 | Phenyl | tert-Butyl | H | Si(Me)$_3$ | Si(Me)$_3$ |
| 197 | Phenyl | tert-Butyl | H | Si(Me)3 | N(p-Tol)$_2$ |
| 198 | Phenyl | tert-Butyl | H | Si(Me)$_3$ | Phenyl |
| 199 | Phenyl | tert-Butyl | H | N(p-Tol)$_2$ | H |
| 200 | Phenyl | tert-Butyl | H | N(p-Tol)$_2$ | Methyl |
| 201 | Phenyl | tert-Butyl | H | N(p-Tol)$_2$ | tert-Butyl |
| 202 | Phenyl | tert-Butyl | H | N(p-Tol)$_2$ | Si(Me)$_3$ |
| 203 | Phenyl | tert-Butyl | H | N(p-Tol)$_2$ | N(p-Tol)$_2$ |
| 204 | Phenyl | tert-Butyl | H | N(p-Tol)$_2$ | Phenyl |
| 205 | Phenyl | tert-Butyl | H | Phenyl | H |
| 206 | Phenyl | tert-Butyl | H | Phenyl | Methyl |
| 207 | Phenyl | tert-Butyl | H | Phenyl | tert-Butyl |
| 208 | Phenyl | tert-Butyl | H | Phenyl | Si(Me)$_3$ |
| 209 | Phenyl | tert-Butyl | H | Phenyl | N(p-Tol)$_2$ |
| 210 | Phenyl | tert-Butyl | H | Phenyl | Phenyl |
| 211 | Phenyl | Si(Me)$_3$ | H | Methyl | H |
| 212 | Phenyl | Si(Me)$_3$ | H | Methyl | Methyl |
| 213 | Phenyl | Si(Me)$_3$ | H | Methyl | tert-Butyl |
| 214 | Phenyl | Si(Me)$_3$ | H | Methyl | Si(Me)$_3$ |
| 215 | Phenyl | Si(Me)$_3$ | H | Methyl | N(p-Tol)$_2$ |
| 216 | Phenyl | Si(Me)$_3$ | H | Methyl | Phenyl |
| 217 | Phenyl | Si(Me)$_3$ | H | tert-Butyl | H |
| 218 | Phenyl | Si(Me)$_3$ | H | tert-Butyl | Methyl |
| 219 | Phenyl | Si(Me)$_3$ | H | tert-Butyl | tert-Butyl |
| 220 | Phenyl | Si(Me)$_3$ | H | tert-Butyl | Si(Me)$_3$ |
| 221 | Phenyl | Si(Me)$_3$ | H | tert-Butyl | N(p-Tol)$_2$ |
| 222 | Phenyl | Si(Me)$_3$ | H | tert-Butyl | Phenyl |
| 223 | Phenyl | Si(Me)$_3$ | H | Si(Me)$_3$ | H |
| 224 | Phenyl | Si(Me)$_3$ | H | Si(Me)$_3$ | Methyl |
| 225 | Phenyl | Si(Me)$_3$ | H | Si(Me)$_3$ | tert-Butyl |
| 226 | Phenyl | Si(Me)$_3$ | H | Si(Me)$_3$ | Si(Me)$_3$ |
| 227 | Phenyl | Si(Me)$_3$ | H | Si(Me)$_3$ | N(p-Tol)$_2$ |
| 228 | Phenyl | Si(Me)3 | H | Si(Me)3 | Phenyl |
| 229 | Phenyl | Si(Me)$_3$ | H | Si(Me)$_3$ | H |
| 230 | Phenyl | Si(Me)$_3$ | H | N(p-Tol)$_2$ | Methyl |
| 231 | Phenyl | Si(Me)$_3$ | H | N(p-Tol)$_2$ | tert-Butyl |
| 232 | Phenyl | Si(Me)$_3$ | H | N(p-Tol)$_2$ | Si(Me)$_3$ |
| 233 | Phenyl | Si(Me)$_3$ | H | N(p-Tol)$_2$ | N(p-Tol)$_2$ |
| 234 | Phenyl | Si(Me)$_3$ | H | N(p-Tol)$_2$ | Phenyl |
| 235 | Phenyl | Si(Me)$_3$ | H | Phenyl | H |
| 236 | Phenyl | Si(Me)$_3$ | H | Phenyl | Methyl |
| 237 | Phenyl | Si(Me)$_3$ | H | Phenyl | tert-Butyl |
| 238 | Phenyl | Si(Me)$_3$ | H | Phenyl | Si(Me)$_3$ |
| 239 | Phenyl | Si(Me)$_3$ | H | Phenyl | N(p-Tol)$_2$ |
| 240 | Phenyl | Si(Me)$_3$ | H | Phenyl | Phenyl |
| 241 | Phenyl | N(p-Tol)$_2$ | H | Methyl | H |
| 242 | Phenyl | N(p-Tol)$_2$ | H | Methyl | Methyl |
| 243 | Phenyl | N(p-Tol)$_2$ | H | Methyl | tert-Butyl |
| 244 | Phenyl | N(p-Tol)$_2$ | H | Methyl | Si(Me)$_3$ |
| 245 | Phenyl | N(p-Tol)$_2$ | H | Methyl | N(p-Tol)$_2$ |
| 246 | Phenyl | N(p-Tol)$_2$ | H | Methyl | Phenyl |
| 247 | Phenyl | N(p-Tol)$_2$ | H | tert-Butyl | H |
| 248 | Phenyl | N(p-Tol)$_2$ | H | tert-Butyl | Methyl |
| 249 | Phenyl | N(p-Tol)$_2$ | H | tert-Butyl | tert-Butyl |
| 250 | Phenyl | N(p-Tol)$_2$ | H | tert-Butyl | Si(Me)$_3$ |
| 251 | Phenyl | N(p-Tol)$_2$ | H | tert-Butyl | N(p-Tol)$_2$ |
| 252 | Phenyl | N(p-Tol)$_2$ | H | tert-Butyl | Phenyl |
| 253 | Phenyl | N(p-Tol)$_2$ | H | Si(Me)$_3$ | H |
| 254 | Phenyl | N(p-Tol)$_2$ | H | Si(Me)$_3$ | Methyl |
| 255 | Phenyl | N(p-Tol)$_2$ | H | Si(Me)$_3$ | tert-Butyl |
| 256 | Phenyl | N(p-Tol)$_2$ | H | Si(Me)$_3$ | Si(Me)$_3$ |
| 257 | Phenyl | N(p-Tol)$_2$ | H | Si(Me)$_3$ | N(p-Tol)$_2$ |
| 258 | Phenyl | N(p-Tol)$_2$ | H | Si(Me)$_3$ | Phenyl |
| 259 | Phenyl | N(p-Tol)$_2$ | H | N(p-Tol)$_2$ | H |
| 260 | Phenyl | N(p-Tol)$_2$ | H | N(p-Tol)$_2$ | Methyl |
| 261 | Phenyl | N(p-Tol)$_2$ | H | N(p-Tol)$_2$ | tert-Butyl |
| 262 | Phenyl | N(p-Tol)$_2$ | H | N(p-Tol)$_2$ | Si(Me)$_3$ |
| 263 | Phenyl | N(p-Tol)$_2$ | H | N(p-Tol)$_2$ | N(p-Tol)$_2$ |
| 264 | Phenyl | N(p-Tol)$_2$ | H | N(p-Tol)$_2$ | Phenyl |
| 265 | Phenyl | N(p-Tol)$_2$ | H | Phenyl | H |
| 266 | Phenyl | N(p-Tol)$_2$ | H | Phenyl | Methyl |
| 267 | Phenyl | N(p-Tol)$_2$ | H | Phenyl | tert-Butyl |
| 268 | Phenyl | N(p-Tol)$_2$ | H | Phenyl | Si(Me)$_3$ |
| 269 | Phenyl | N(p-Tol)$_2$ | H | Phenyl | N(p-Tol)$_2$ |
| 270 | Phenyl | N(p-Tol)$_2$ | H | Phenyl | Phenyl |
| 271 | Phenyl | Phenyl | H | Methyl | H |
| 272 | Phenyl | Phenyl | H | Methyl | Methyl |
| 273 | Phenyl | Phenyl | H | Methyl | tert-Butyl |
| 274 | Phenyl | Phenyl | H | Methyl | Si(Me)$_3$ |
| 275 | Phenyl | Phenyl | H | Methyl | N(p-Tol)$_2$ |
| 276 | Phenyl | Phenyl | H | Methyl | Phenyl |
| 277 | Phenyl | Phenyl | H | tert-Butyl | H |
| 278 | Phenyl | Phenyl | H | tert-Butyl | Methyl |
| 279 | Phenyl | Phenyl | H | tert-Butyl | tert-Butyl |
| 280 | Phenyl | Phenyl | H | tert-Butyl | Si(Me)$_3$ |
| 281 | Phenyl | Phenyl | H | tert-Butyl | N(p-Tol)$_2$ |
| 282 | Phenyl | Phenyl | H | tert-Butyl | Phenyl |
| 283 | Phenyl | Phenyl | H | Si(Me)$_3$ | H |
| 284 | Phenyl | Phenyl | H | Si(Me)$_3$ | Methyl |
| 285 | Phenyl | Phenyl | H | Si(Me)$_3$ | tert-Butyl |
| 286 | Phenyl | Phenyl | H | Si(Me)$_3$ | Si(Me)$_3$ |
| 287 | Phenyl | Phenyl | H | Si(Me)$_3$ | N(p-Tol)$_2$ |
| 288 | Phenyl | Phenyl | H | Si(Me)$_3$ | Phenyl |
| 289 | Phenyl | Phenyl | H | N(p-Tol)$_2$ | H |
| 290 | Phenyl | Phenyl | H | N(p-Tol)$_2$ | Methyl |
| 291 | Phenyl | Phenyl | H | N(p-Tol)$_2$ | tert-Butyl |
| 292 | Phenyl | Phenyl | H | N(p-Tol)$_2$ | Si(Me)$_3$ |

TABLE 1-continued

Preferred structures of the formula (8)

| No. | Ar | Rc | Rd | Ra | Rb |
|---|---|---|---|---|---|
| 293 | Phenyl | Phenyl | H | N(p-Tol)$_2$ | N(p-Tol)$_2$ |
| 294 | Phenyl | Phenyl | H | N(p-Tol)$_2$ | Phenyl |
| 295 | Phenyl | Phenyl | H | Phenyl | H |
| 296 | Phenyl | Phenyl | H | Phenyl | Methyl |
| 297 | Phenyl | Phenyl | H | Phenyl | tert-Butyl |
| 298 | Phenyl | Phenyl | H | Phenyl | Si(Me)$_3$ |
| 299 | Phenyl | Phenyl | H | Phenyl | N(p-Tol)$_2$ |
| 300 | Phenyl | Phenyl | H | Phenyl | Phenyl |
| 301 | 1-Naphthyl | H | — | Methyl | H |
| 302 | 1-Naphthyl | H | — | Methyl | Methyl |
| 303 | 1-Naphthyl | H | — | Methyl | tert-Butyl |
| 304 | 1-Naphthyl | H | — | Methyl | Si(Me)$_3$ |
| 305 | 1-Naphthyl | H | — | Methyl | N(p-Tol)$_2$ |
| 306 | 1-Naphthyl | H | — | Methyl | Phenyl |
| 307 | 1-Naphthyl | H | — | tert-Butyl | H |
| 308 | 1-Naphthyl | H | — | tert-Butyl | Methyl |
| 309 | 1-Naphthyl | H | — | tert-Butyl | tert-Butyl |
| 310 | 1-Naphthyl | H | — | tert-Butyl | Si(Me)$_3$ |
| 311 | 1-Naphthyl | H | — | tert-Butyl | N(p-Tol)$_2$ |
| 312 | 1-Naphthyl | H | — | tert-Butyl | Phenyl |
| 313 | 1-Naphthyl | H | — | Si(Me)$_3$ | H |
| 314 | 1-Naphthyl | H | — | Si(Me)$_3$ | Methyl |
| 315 | 1-Naphthyl | H | — | Si(Me)$_3$ | tert-Butyl |
| 316 | 1-Naphthyl | H | — | Si(Me)$_3$ | Si(Me)$_3$ |
| 317 | 1-Naphthyl | H | — | Si(Me)$_3$ | N(p-Tol)2 |
| 318 | 1-Naphthyl | H | — | Si(Me)$_3$ | N(p-Tol)$_2$ |
| 319 | 1-Naphthyl | H | — | N(p-Tol)$_2$ | H |
| 320 | 1-Naphthyl | H | — | N(p-Tol)$_2$ | Methyl |
| 321 | 1-Naphthyl | H | — | N(p-Tol)$_2$ | tert-Butyl |
| 322 | 1-Naphthyl | H | — | N(p-Tol)$_2$ | Si(Me)$_3$ |
| 323 | 1-Naphthyl | H | — | N(p-Tol)$_2$ | N(p-Tol)$_2$ |
| 324 | 1-Naphthyl | H | — | N(p-Tol)$_2$ | Phenyl |
| 325 | 1-Naphthyl | H | — | Phenyl | H |
| 326 | 1-Naphthyl | H | — | Phenyl | Methyl |
| 327 | 1-Naphthyl | H | — | Phenyl | tert-Butyl |
| 328 | 1-Naphthyl | H | — | Phenyl | Si(Me)$_3$ |
| 329 | 1-Naphthyl | H | — | Phenyl | N(p-Tol)$_2$ |
| 330 | 1-Naphthyl | H | — | Phenyl | Phenyl |
| 331 | 1-Naphthyl | Methyl | — | Methyl | H |
| 332 | 1-Naphthyl | Methyl | — | Methyl | Methyl |
| 333 | 1-Naphthyl | Methyl | — | Methyl | tert-Butyl |
| 334 | 1-Naphthyl | Methyl | — | Methyl | Si(Me)$_3$ |
| 335 | 1-Naphthyl | Methyl | — | Methyl | N(p-Tol)$_2$ |
| 336 | 1-Naphthyl | Methyl | — | Methyl | Phenyl |
| 337 | 1-Naphthyl | Methyl | — | tert-Butyl | H |
| 338 | 1-Naphthyl | Methyl | — | tert-Butyl | Methyl |
| 339 | 1-Naphthyl | Methyl | — | tert-Butyl | tert-Butyl |
| 340 | 1-Naphthyl | Methyl | — | tert-Butyl | Si(Me)$_3$ |
| 341 | 1-Naphthyl | Methyl | — | tert-Butyl | N(p-Tol)$_2$ |
| 342 | 1-Naphthyl | Methyl | — | tert-Butyl | Phenyl |
| 343 | 1-Naphthyl | Methyl | — | Si(Me)$_3$ | H |
| 344 | 1-Naphthyl | Methyl | — | Si(Me)$_3$ | Methyl |
| 345 | 1-Naphthyl | Methyl | — | Si(Me)$_3$ | tert-Butyl |
| 346 | 1-Naphthyl | Methyl | — | Si(Me)$_3$ | Si(Me)$_3$ |
| 347 | 1-Naphthyl | Methyl | — | Si(Me)$_3$ | N(p-Tol)$_2$ |
| 348 | 1-Naphthyl | Methyl | — | Si(Me)$_3$ | Phenyl |
| 349 | 1-Naphthyl | Methyl | — | N(p-Tol)$_2$ | H |
| 350 | 1-Naphthyl | Methyl | — | N(p-Tol)$_2$ | Methyl |
| 351 | 1-Naphthyl | Methyl | — | N(p-Tol)$_2$ | tert-Butyl |
| 352 | 1-Naphthyl | Methyl | — | N(p-Tol)$_2$ | Si(Me)$_3$ |
| 353 | 1-Naphthyl | Methyl | — | N(p-Tol)$_2$ | N(p-Tol)$_2$ |
| 354 | 1-Naphthyl | Methyl | — | N(p-Tol)$_2$ | Phenyl |
| 355 | 1-Naphthyl | Methyl | — | Phenyl | H |
| 356 | 1-Naphthyl | Methyl | — | Phenyl | Methyl |
| 357 | 1-Naphthyl | Methyl | — | Phenyl | tert-Butyl |
| 358 | 1-Naphthyl | Methyl | — | Phenyl | Si(Me)$_3$ |
| 359 | 1-Naphthyl | Methyl | — | Phenyl | N(p-Tol)$_2$ |
| 360 | 1-Naphthyl | Methyl | — | Phenyl | Phenyl |
| 361 | 2-Naphthyl | — | — | Methyl | H |
| 362 | 2-Naphthyl | — | — | Methyl | Methyl |
| 363 | 2-Naphthyl | — | — | Methyl | tert-Butyl |
| 364 | 2-Naphthyl | — | — | Methyl | Si(Me)$_3$ |
| 365 | 2-Naphthyl | — | — | Methyl | N(p-Tol)$_2$ |
| 366 | 2-Naphthyl | — | — | Methyl | Phenyl |
| 367 | 2-Naphthyl | — | — | tert-Butyl | H |
| 368 | 2-Naphthyl | — | — | tert-Butyl | Methyl |
| 369 | 2-Naphthyl | — | — | tert-Butyl | tert-Butyl |
| 370 | 2-Naphthyl | — | — | tert-Butyl | Si(Me)$_3$ |
| 371 | 2-Naphthyl | — | — | tert-Butyl | N(p-Tol)$_2$ |
| 372 | 2-Naphthyl | — | — | tert-Butyl | Phenyl |
| 373 | 2-Naphthyl | — | — | Si(Me)$_3$ | H |
| 374 | 2-Naphthyl | — | — | Si(Me)$_3$ | Methyl |
| 375 | 2-Naphthyl | — | — | Si(Me)$_3$ | tert-Butyl |
| 376 | 2-Naphthyl | — | — | Si(Me)$_3$ | Si(Me)$_3$ |
| 377 | 2-Naphthyl | — | — | Si(Me)$_3$ | N(p-Tol)$_2$ |
| 378 | 2-Naphthyl | — | — | Si(Me)$_3$ | Phenyl |
| 379 | 2-Naphthyl | — | — | N(p-Tol)$_2$ | H |
| 380 | 2-Naphthyl | — | — | N(p-Tol)$_2$ | Methyl |
| 381 | 2-Naphthyl | — | — | N(p-Tol)$_2$ | tert-Butyl |
| 382 | 2-Naphthyl | — | — | N(p-Tol)$_2$ | Si(Me)$_3$ |
| 383 | 2-Naphthyl | — | — | N(p-Tol)$_2$ | N(p-Tol)$_2$ |
| 384 | 2-Naphthyl | — | — | N(p-Tol)$_2$ | Phenyl |
| 385 | 2-Naphthyl | — | — | Phenyl | H |
| 386 | 2-Naphthyl | — | — | Phenyl | Methyl |
| 387 | 2-Naphthyl | — | — | Phenyl | tert-Butyl |
| 388 | 2-Naphthyl | — | — | Phenyl | Si(Me)$_3$ |
| 389 | 2-Naphthyl | — | — | Phenyl | N(p-Tol)$_2$ |
| 390 | 2-Naphthyl | — | — | Phenyl | Phenyl |
| 391 | 9-Anthryl | 1-Naphthyl | — | Methyl | H |
| 392 | 9-Anthryl | 1-Naphthyl | — | Methyl | Methyl |
| 393 | 9-Anthryl | 1-Naphthyl | — | Methyl | tert-Butyl |
| 394 | 9-Anthryl | 1-Naphthyl | — | Methyl | Si(Me)$_3$ |
| 395 | 9-Anthryl | 1-Naphthyl | — | Methyl | N(p-Tol)$_2$ |
| 396 | 9-Anthryl | 1-Naphthyl | — | Methyl | Phenyl |
| 397 | 9-Anthryl | 1-Naphthyl | — | tert-Butyl | H |
| 398 | 9-Anthryl | 1-Naphthyl | — | tert-Butyl | Methyl |
| 399 | 9-Anthryl | 1-Naphthyl | — | tert-Butyl | tert-Butyl |
| 400 | 9-Anthryl | 1-Naphthyl | — | tert-Butyl | Si(Me)$_3$ |
| 401 | 9-Anthryl | 1-Naphthyl | — | tert-Butyl | N(p-Tol)$_2$ |
| 402 | 9-Anthryl | 1-Naphthyl | — | tert-Butyl | Phenyl |
| 403 | 9-Anthryl | 1-Naphthyl | — | Si(Me)$_3$ | H |
| 404 | 9-Anthryl | 1-Naphthyl | — | Si(Me)$_3$ | Methyl |
| 405 | 9-Anthryl | 1-Naphthyl | — | Si(Me)$_3$ | tert-Butyl |
| 406 | 9-Anthryl | 1-Naphthyl | — | Si(Me)$_3$ | Si(Me)$_3$ |
| 407 | 9-Anthryl | 1-Naphthyl | — | Si(Me)$_3$ | N(p-Tol)$_2$ |
| 408 | 9-Anthryl | 1-Naphthyl | — | Si(Me)$_3$ | Phenyl |
| 409 | 9-Anthryl | 1-Naphthyl | — | N(p-Tol)$_2$ | H |
| 410 | 9-Anthryl | 1-Naphthyl | — | N(p-Tol)$_2$ | Methyl |
| 411 | 9-Anthryl | 1-Naphthyl | — | N(p-Tol)$_2$ | tert-Butyl |
| 412 | 9-Anthryl | 1-Naphthyl | — | N(p-Tol)$_2$ | Si(Me)$_3$ |
| 413 | 9-Anthryl | 1-Naphthyl | — | N(p-Tol)$_2$ | N(p-Tol)$_2$ |
| 414 | 9-Anthryl | 1-Naphthyl | — | N(p-Tol)$_2$ | Phenyl |
| 415 | 9-Anthryl | 1-Naphthyl | — | Phenyl | H |
| 416 | 9-Anthryl | 1-Naphthyl | — | Phenyl | Methyl |
| 417 | 9-Anthryl | 1-Naphthyl | — | Phenyl | tert-Butyl |
| 418 | 9-Anthryl | 1-Naphthyl | — | Phenyl | Si(Me)$_3$ |
| 419 | 9-Anthryl | 1-Naphthyl | — | Phenyl | N(p-Tol)$_2$ |
| 420 | 9-Anthryl | 1-Naphthyl | — | Phenyl | Phenyl |
| 421 | 9-Anthryl | 2-Naphthyl | — | Methyl | H |
| 422 | 9-Anthryl | 2-Naphthyl | — | Methyl | Methyl |
| 423 | 9-Anthryl | 2-Naphthyl | — | Methyl | tert-Butyl |
| 424 | 9-Anthryl | 2-Naphthyl | — | Methyl | Si(Me)$_3$ |
| 425 | 9-Anthryl | 2-Naphthyl | — | Methyl | N(p-Tol)$_2$ |
| 426 | 9-Anthryl | 2-Naphthyl | — | Methyl | Phenyl |
| 427 | 9-Anthryl | 2-Naphthyl | — | tert-Butyl | H |
| 428 | 9-Anthryl | 2-Naphthyl | — | tert-Butyl | Methyl |
| 429 | 9-Anthryl | 2-Naphthyl | — | tert-Butyl | tert-Butyl |
| 430 | 9-Anthryl | 2-Naphthyl | — | tert-Butyl | Si(Me)$_3$ |
| 431 | 9-Anthryl | 2-Naphthyl | — | tert-Butyl | N(p-Tol)$_2$ |
| 432 | 9-Anthryl | 2-Naphthyl | — | tert-Butyl | Phenyl |
| 433 | 9-Anthryl | 2-Naphthyl | — | Si(Me)$_3$ | H |
| 434 | 9-Anthryl | 2-Naphthyl | — | Si(Me)$_3$ | Methyl |
| 435 | 9-Anthryl | 2-Naphthyl | — | Si(Me)$_3$ | tert-Butyl |
| 436 | 9-Anthryl | 2-Naphthyl | — | Si(Me)$_3$ | Si(Me)$_3$ |
| 437 | 9-Anthryl | 2-Naphthyl | — | Si(Me)$_3$ | N(p-Tol)$_2$ |
| 438 | 9-Anthryl | 2-Naphthyl | — | Si(Me)$_3$ | Phenyl |
| 439 | 9-Anthryl | 2-Naphthyl | — | N(p-Tol)$_2$ | H |
| 440 | 9-Anthryl | 2-Naphthyl | — | N(p-Tol)$_2$ | Methyl |

TABLE 1-continued

Preferred structures of the formula (8)

| No. | Ar | Rc | Rd | Ra | Rb |
|---|---|---|---|---|---|
| 441 | 9-Anthryl | 2-Naphthyl | — | N(p-Tol)$_2$ | tert-Butyl |
| 442 | 9-Anthryl | 2-Naphthyl | — | N(p-Tol)$_2$ | Si(Me)$_3$ |
| 443 | 9-Anthryl | 2-Naphthyl | — | N(p-Tol)$_2$ | N(p-Tol)$_2$ |
| 444 | 9-Anthryl | 2-Naphthyl | — | N(p-Tol)$_2$ | Phenyl |
| 445 | 9-Anthryl | 2-Naphthyl | — | Phenyl | H |
| 446 | 9-Anthryl | 2-Naphthyl | — | Phenyl | Methyl |
| 447 | 9-Anthryl | 2-Naphthyl | — | Phenyl | tert-Butyl |
| 448 | 9-Anthryl | 2-Naphthyl | — | Phenyl | Si(Me)$_3$ |
| 449 | 9-Anthryl | 2-Naphthyl | — | Phenyl | N(p-Tol)$_2$ |
| 450 | 9-Anthryl | 2-Naphthyl | — | Phenyl | Phenyl |
| 451 | 9-Anthryl | N(p-Tol)$_2$ | — | Methyl | H |
| 452 | 9-Anthryl | N(p-Tol)$_2$ | — | Methyl | Methyl |
| 453 | 9-Anthryl | N(p-Tol)$_2$ | — | Methyl | tert-Butyl |
| 454 | 9-Anthryl | N(p-Tol)$_2$ | — | Methyl | Si(Me)$_3$ |
| 455 | 9-Anthryl | N(p-Tol)$_2$ | — | Methyl | N(p-Tol)$_2$ |
| 456 | 9-Anthryl | N(p-Tol)$_2$ | — | Methyl | Phenyl |
| 457 | 9-Anthryl | N(p-Tol)$_2$ | — | tert-Butyl | H |
| 458 | 9-Anthryl | N(p-Tol)$_2$ | — | tert-Butyl | Methyl |
| 459 | 9-Anthryl | N(p-Tol)$_2$ | — | tert-Butyl | tert-Butyl |
| 460 | 9-Anthryl | N(p-Tol)$_2$ | — | tert-Butyl | Si(Me)$_3$ |
| 461 | 9-Anthryl | N(p-Tol)$_2$ | — | tert-Butyl | N(p-Tol)$_2$ |
| 462 | 9-Anthryl | N(p-Tol)$_2$ | — | tert-Butyl | Phenyl |
| 463 | 9-Anthryl | N(p-Tol)$_2$ | — | Si(Me)$_3$ | H |
| 464 | 9-Anthryl | N(p-Tol)$_2$ | — | Si(Me)$_3$ | Methyl |
| 465 | 9-Anthryl | N(p-Tol)$_2$ | — | Si(Me)$_3$ | tert-Butyl |
| 466 | 9-Anthryl | N(p-Tol)$_2$ | — | Si(Me)$_3$ | Si(Me)$_3$ |
| 467 | 9-Anthryl | N(p-Tol)$_2$ | — | Si(Me)$_3$ | N(p-Tol)$_2$ |
| 468 | 9-Anthryl | N(p-Tol)$_2$ | — | Si(Me)$_3$ | Phenyl |
| 469 | 9-Anthryl | N(p-Tol)$_2$ | — | N(p-Tol)$_2$ | H |
| 470 | 9-Anthryl | N(p-Tol)$_2$ | — | N(p-Tol)$_2$ | Methyl |
| 471 | 9-Anthryl | N(p-Tol)$_2$ | — | N(p-Tol)$_2$ | tert-Butyl |
| 472 | 9-Anthryl | N(p-Tol)$_2$ | — | N(p-Tol)$_2$ | Si(Me)$_3$ |
| 473 | 9-Anthryl | N(p-Tol)$_2$ | — | N(p-Tol)$_2$ | N(p-Tol)$_2$ |
| 474 | 9-Anthryl | N(p-Tol)$_2$ | — | N(p-Tol)$_2$ | Phenyl |
| 475 | 9-Anthryl | N(p-Tol)$_2$ | — | Phenyl | H |
| 476 | 9-Anthryl | N(p-Tol)$_2$ | — | Phenyl | Methyl |
| 477 | 9-Anthryl | N(p-Tol)$_2$ | — | Phenyl | tert-Butyl |
| 478 | 9-Anthryl | N(p-Tol)$_2$ | — | Phenyl | Si(Me)$_3$ |
| 479 | 9-Anthryl | N(p-Tol)$_2$ | — | Phenyl | N(p-Tol)$_2$ |
| 480 | 9-Anthryl | N(p-Tol)$_2$ | — | Phenyl | Phenyl |
| 481 | 9-Anthryl | Phenyl | — | Methyl | H |
| 482 | 9-Anthryl | Phenyl | — | Methyl | Methyl |
| 483 | 9-Anthryl | Phenyl | — | Methyl | tert-Butyl |
| 484 | 9-Anthryl | Phenyl | — | Methyl | Si(Me)$_3$ |
| 485 | 9-Anthryl | Phenyl | — | Methyl | N(p-Tol)$_2$ |
| 486 | 9-Anthryl | Phenyl | — | Methyl | Phenyl |
| 487 | 9-Anthryl | Phenyl | — | tert-Butyl | H |
| 488 | 9-Anthryl | Phenyl | — | tert-Butyl | Methyl |
| 489 | 9-Anthryl | Phenyl | — | tert-Butyl | tert-Butyl |
| 490 | 9-Anthryl | Phenyl | — | tert-Butyl | Si(Me)$_3$ |
| 491 | 9-Anthryl | Phenyl | — | tert-Butyl | N(p-Tol)$_2$ |
| 492 | 9-Anthryl | Phenyl | — | tert-Butyl | Phenyl |
| 493 | 9-Anthryl | Phenyl | — | Si(Me)$_3$ | H |
| 494 | 9-Anthryl | Phenyl | — | Si(Me)$_3$ | Methyl |
| 495 | 9-Anthryl | Phenyl | — | Si(Me)$_3$ | tert-Butyl |
| 496 | 9-Anthryl | Phenyl | — | Si(Me)$_3$ | Si(Me)$_3$ |
| 497 | 9-Anthryl | Phenyl | — | Si(Me)$_3$ | N(p-Tol)$_2$ |
| 498 | 9-Anthryl | Phenyl | — | Si(Me)$_3$ | Phenyl |
| 499 | 9-Anthryl | Phenyl | — | N(p-Tol)$_2$ | H |
| 500 | 9-Anthryl | Phenyl | — | N(p-Tol)$_2$ | Methyl |
| 501 | 9-Anthryl | Phenyl | — | N(p-Tol)$_2$ | tert-Butyl |
| 502 | 9-Anthryl | Phenyl | — | N(p-Tol)$_2$ | Si(Me)$_3$ |
| 503 | 9-Anthryl | Phenyl | — | N(p-Tol)$_2$ | N(p-Tol)$_2$ |
| 504 | 9-Anthryl | Phenyl | — | N(p-Tol)$_2$ | Phenyl |
| 505 | 9-Anthryl | Phenyl | — | Phenyl | H |
| 506 | 9-Anthryl | Phenyl | — | Phenyl | Methyl |
| 507 | 9-Anthryl | Phenyl | — | Phenyl | tert-Butyl |
| 508 | 9-Anthryl | Phenyl | — | Phenyl | Si(Me)$_3$ |
| 509 | 9-Anthryl | Phenyl | — | Phenyl | N(p-Tol)$_2$ |
| 510 | 9-Anthryl | Phenyl | — | Phenyl | Phenyl |

The compounds can be synthesised, for example, starting from 2,6-dichloro- or dibromoanthraquinone. This is reacted with arylboronic acids in a Suzuki coupling to give the corresponding 2,6-diarylanthraquinone. This can be reacted with an aromatic Grignard reagent in a further step and then with a reducing agent, for example tin(II) chloride, to give 2,6,9,10-tetraarylanthracene.

The present invention therefore furthermore relates to a process for the preparation of compounds of the formula (1) by reaction of 2,6-dihaloanthraquinone or an analogous sulfonic acid derivative with a boronic acid derivative of the group Ar with palladium catalysis, followed by reaction with a corresponding ortho-substituted organometallic phenyl derivative and reduction.

The process thus takes place in accordance with the following scheme:

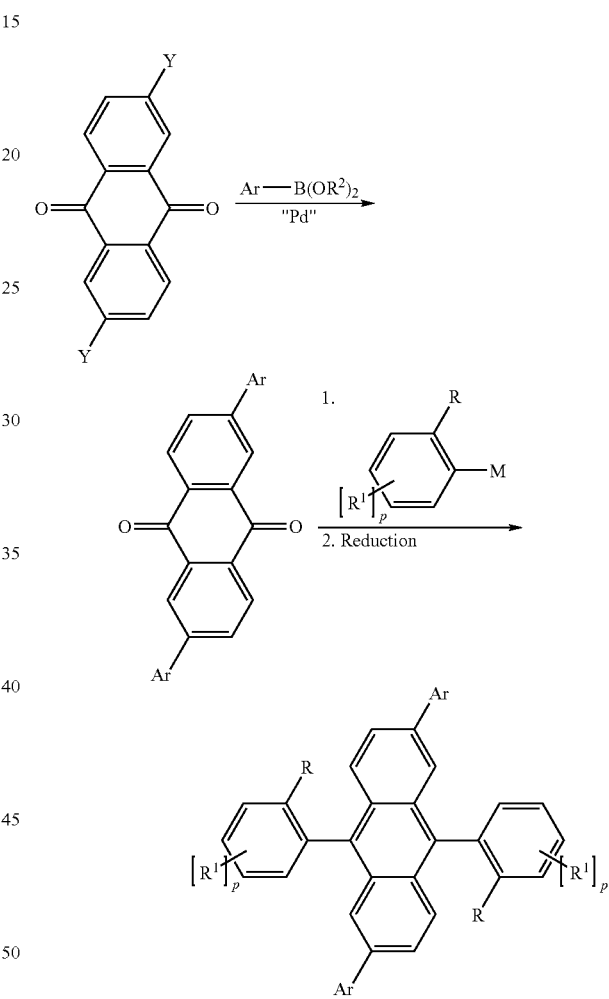

Ar, R, $R^1$, $R^2$ and p here have the same meanings as described above. Y stands for chlorine, bromine or iodine, preferably bromine, or for a group of the formula $OSO_2R^2$. M stands for an electropositive metal, in particular lithium, magnesium or zinc, and, in the case of a divalent metal, also contains a further organic group or a group Y. The way in which a Suzuki coupling (first reaction step) is carried out and which palladium catalysts are particularly suitable for this purpose is known to the person skilled in the art of organic synthesis. The reducing agent employed in the second reaction step is preferably tin(II) chloride.

The compounds of the formula (1) can be employed in organic electroluminescent devices. They are particularly suitable for use as host material for fluorescent emitters, but may each of which may, depending on the substitution pattern, also be employed as emitter, as hole-transport material, as hole-blocking material and/or as electron-transport material.

The invention therefore furthermore relates to the use of compounds of the formula (1) in organic electronic devices, in particular in organic electroluminescent devices, in particular as host material, as emitter, as hole-transport material, as hole-blocking material and/or as electron-transport material.

The invention furthermore relates to organic electronic devices, in particular organic electroluminescent devices, comprising anode, cathode and at least one emitting layer, where at least one layer comprises at least one compound of the formula (1). The layer which comprises the compound of the formula (1) is preferably an emitting layer, a hole-transport layer, a hole-injection layer, a hole-blocking layer or an electron-transport layer.

Apart from the cathode, anode and emitting layer (or emitting layers), the organic electroluminescent device may also comprise further layers. These may be, for example: hole-injection layer, hole-transport layer, hole-blocking layer, electron-transport layer, electron-injection layer and/or a charge-generation layer (T. Matsumoto et al., *Multiphoton Organic EL Device Having Charge Generation Layer*, IDMC 2003, Taiwan; Session 21 OLED (5)). The materials in these layers may also be doped. Each of these layers does not necessarily have to be present. Suitable hole-transport materials are, for example, aromatic amines, as usually used in accordance with the prior art and which may also be p-doped. Suitable electron-transport materials are, for example, metal chelate complexes, for example $AlQ_3$, compounds based on electron-deficient heterocycles, for example triazine derivatives, or compounds containing aromatic carbonyls or phosphine oxides, as described, for example, in WO 05/084081 and WO 05/084082, which may in each case also be n-doped. Suitable electron-injection materials are, in particular, fluorides and oxides of the alkali and alkaline earth metals, for example NaF, $BaF_2$, $CaF_2$, LiF or $Li_2O$.

In a preferred embodiment of the invention, the compound of the formula (1) is employed as host material, in particular for fluorescent emitters, and/or as electron-transport material and/or as hole-blocking material. This is the case, in particular, if the compound does not contain any substituents of the formula $N(Ar^1)_2$.

A host material is taken to mean the component in a system comprising host and dopant (binary mixture) which is present in the system in the higher proportion. In a system comprising a host and a plurality of dopants (ternary and higher mixtures), the host is taken to mean the component whose proportion is the highest in the mixture.

The proportion of the host material of the formula (1) in the emitting layer is between 50.0 and 99.9% by weight, preferably between 80.0 and 99.5% by weight, particularly preferably between 90.0 and 99.0% by weight. Correspondingly, the proportion of the dopant in the emitting layer is between 0.1 and 50.0% by weight, preferably between 0.5 and 20.0% by weight, particularly preferably between 1.0 and 10.0% by weight.

Preferred dopants are selected from the class of the aromatic anthracenamines, the aromatic anthracenediamines, the aromatic pyrenamines, the aromatic pyrenediamines, the monostyrylamines, the distyrylamines, the tristyrylamines, the tetrastyrylamines, the styrylphosphines, the styryl ethers and the arylamines. An aromatic anthracenamine is taken to mean a compound in which a diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines and pyrenediamines are defined analogously, with the diarylamino groups preferably being bonded to the pyrene in the 1-position or in the 1,6-position. A monostyrylamine is taken to mean a compound which contains a substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one aryl group here is preferably a condensed aryl group having at least three rings. The styryl groups are particularly preferably stilbenes, which may also be further substituted. Particularly preferred dopants are selected from the classes of the tristilbenamines, the aromatic stilbenediamines, the anthracenediamines and the pyrenediamines. Very particularly preferred dopants are selected from the class of the tristyrylamines. Examples of dopants of this type are substituted or unsubstituted tristilbenamines or the dopants described in WO 06/000388, WO 06/058737 and WO 06/000389.

In a further embodiment of the invention, the organic electroluminescent device comprises a plurality of emitting layers, where at least one of these layers comprises at least one compound of the formula (1). These emission layers particularly preferably have in total a plurality of emission maxima between 380 nm and 750 nm, resulting overall in white emission, i.e. at least one further emitting compound which is able to fluoresce or phosphoresce and emits yellow, orange or red light is used in the further emitting layer(s). Preference is given to three-layer systems, where at least one of these layers comprises at least one compound of the formula (1) and where the three layers exhibit blue, green and orange or red emission (for the basic structure, see, for example, WO 05/011013). Emitters which have broad-band emission bands and thus exhibit white emission are likewise suitable for white emission.

In addition to the compounds of the formula (1) and the dopant(s), further substances, for example hole- or electron-transport materials, may also be present in the emitting layer.

If the symbol R stands for an $N(Ar^1)_2$ group and/or at least one substituent $R^1$ on the Ar group or in another position stands for an $N(Ar^1)_2$ group, the compound of the formula (1) is particularly suitable as emitting compound and/or as hole-transport material, as described in more detail below.

If the compound of the formula (1) is employed as hole-transport material, it is preferably employed in a hole-transport layer and/or in a hole-injection layer. For the purposes of this invention, a hole-injection layer is a layer which is directly adjacent to the anode. For the purposes of this invention, a hole-transport layer is a layer which is located between a hole-injection layer and an emission layer. If the compounds of the formula (1) are used as hole-transport or hole-injection material, it may be preferred for them to be doped with electron-acceptor compounds, for example with $F_4$-TCNQ or with compounds as described in EP 1476881 or EP 1596445.

If the compound of the formula (1) is employed as emitting compound, it is preferably employed in combination with a host material.

The proportion of the emitting compound of the formula (1) in the mixture of the emitting layer is between 0.1 and 50.0% by weight, preferably between 0.5 and 20.0% by weight, particularly preferably between 1.0 and 10.0% by weight. Correspondingly, the proportion of the host material in the layer is between 50.0 and 99.9% by weight, preferably between 80.0 and 99.5% by weight, particularly preferably between 90.0 and 99.0% by weight.

Suitable host materials are various classes of substance. Preferred host materials are selected from the classes of the oligoarylenes (for example 2, 2',7,7'-tetraphenylspirobifluorene as described in EP 676461 or dinaphthylanthracene), in particular the oligoarylenes containing condensed aromatic groups, the oligoarylenevinylenes (for example DPVBi or spiro-DPVBi as described in EP 676461), the polypodal metal complexes (for example as described in WO 04/081017), the hole-conducting compounds (for example as described in WO 04/058911), the electron-conducting compounds, in particular ketones, phosphine oxides, sulfoxides, etc. (for example as described in WO 05/084081 or WO 05/084082), the atropisomers (for example as described in WO 06/048268) or the boronic acid derivatives (for example as described in WO 06/117052). Particularly preferred host materials are selected from the classes of the oligoarylenes containing naphthalene, anthracene and/or pyrene or atropisomers of these compounds, the oligoarylenevinylenes, the ketones, the phosphine oxides and the sulfoxides. Very particularly preferred host materials are selected from the classes of the oligoarylenes containing anthracene and/or pyrene or atropisomers of these compounds, the phosphine oxides and the sulfoxides.

Preference is furthermore given to an organic electroluminescent device, characterised in that one or more layers are coated by means of a sublimation process, in which the materials are vapour-deposited in vacuum sublimation units at a pressure of less than $10^{-5}$ mbar, preferably less than $10^{-6}$ mbar, particularly preferably less than $10^{-7}$ mbar.

Preference is likewise given to an organic electroluminescent device, characterised in that one or more layers are coated by the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light-induced thermal imaging, thermal transfer printing) or ink-jet printing. Soluble compounds of the formula (1) are necessary for this purpose. The compounds according to the invention are therefore very highly suitable for processing from solution since, due to the substitution, they have high solubility in organic solvents.

The organic electroluminescent devices according to the invention have the following surprising properties:
1. The compounds according to the invention have high thermal stability and in particular a high glass-transition temperature.
2. The compounds according to the invention exhibit high efficiency, a good lifetime and good colour coordinates on use in OLEDs.
3. The compounds according to the invention have good solubility in organic solvents, which simplifies the preparation and processing of these compounds.
4. The compounds according to the invention have high redox stability (high stability to holes and electrons).
5. The film-formation properties of the compounds according to the invention are very good.

The present application text is directed to the use of compounds according to the invention in relation to OLEDs and the corresponding displays.

In spite of this restriction of the description, it is possible for the person skilled in the art, without further inventive step, also to use the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), organic photo receptors, light-emitting electrochemical cells (LECs) or also organic laser diodes (O-lasers), to mention but a few applications.

The present invention furthermore relates to the use of the compounds according to the invention in the corresponding devices and to these devices themselves.

The invention is explained in greater detail by the following examples, without wishing to restrict it thereby.

EXAMPLES

The following syntheses are carried out under a protective-gas atmosphere, unless indicated otherwise. The starting materials can be purchased from ALDRICH or ABCR (palladium(II) acetate, tri-o-tolyl-phosphine, di-tert-butylchlorophosphine, bromides, amines, inorganics, solvents). 2,6-Dibromoanthraquinone is prepared by the method of Lee et al., *Org. Lett.* 2005, 7(2), 323; 2-trimethylsilylbromobenzene is prepared by the method of Klusener et al., *Org. Chem.* 1990, 55(4), 1311; pinacolyl 10-(4-methylnaphth-1-yl)anthracene-9-boronate is prepared in accordance with EP 05009643.7; 1-bromo-2-(1-methyl-1-phenylethyl)benzene is prepared by the method of Sigmundova et al., *Synth. Commun.* 2004, 34(20), 3667.

Example 1

2,6,9,10-Tetra-o-tolylanthracene a) 2,6-Bis-o-tolylanthraquinone

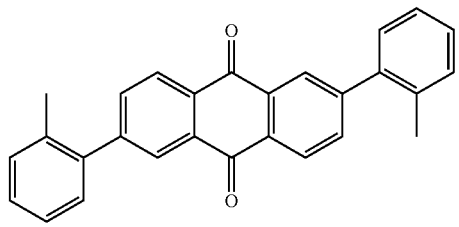 [SMILES: Cc1ccccc1-c1ccc2c(c1)C(=O)c1ccc(-c3ccccc3C)cc1C2=O]

A suspension of 28.7 g (100 mmol) of 2,6-dibromoanthraquinone, 32.6 g (240 mmol) of o-tolylboronic acid, 89.2 g (420 mmol) of potassium phosphate, 1.8 g (8 mmol) of tri-o-tolylphosphine and 225 mg (1 mmol) of palladium(II) acetate in a mixture of 200 ml of dioxane, 400 ml of toluene and 500 ml of water is refluxed for 16 h. After cooling, the solid is filtered off with suction, washed three times with 100 ml of water each time and three times with 100 ml of ethanol each time, dried in vacuo and subsequently recrystallised twice from DMF. Yield: 33.0 g (85 mmol), 84.9% of theory, purity: 98% according to NMR.

b) 2,6,9,1-Tetra-o-tolylanthracene

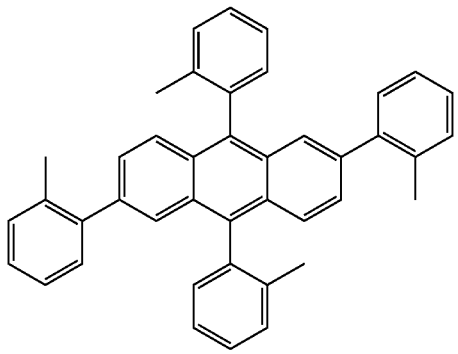 [SMILES: Cc1ccccc1-c1ccc2c(-c3ccccc3C)c3cc(-c4ccccc4C)ccc3c(-c3ccccc3C)c2c1]

The corresponding Grignard reagent is prepared from 3.7 g (153 mmol) of magnesium and 18.0 ml (150 mmol) of 2-bromotoluene in 500 ml of THF. 19.4 g (50 mmol) of 2,6-bis-o-tolylanthraquinone are added to the Grignard reagent. The reaction mixture is subsequently refluxed for 16 h. After cooling, 30 ml of ethanol are added, the solvent is removed in vacuo, the residue is taken up in 300 ml of DMF and warmed to 60° C., and 8.9 g (65 mmol) of tin(II) chloride are then added in portions with vigorous stirring (note: exothermic reaction!). The mixture is subsequently stirred at 60° C. for a further 2 h. After cooling, 500 ml of 2.5N hydrochloric acid are added, and the solid is filtered off with suction. The solid is washed three times with 100 ml of 2.5N hydrochloric acid each time, three times with 100 ml of water each time and three times with 100 ml of ethanol each time, dried in vacuo and subsequently recrystallised three times from acetic acid and twice from DMF. Sublimation p=1×10$^{-5}$ mbar, T=335° C. Yield: 19.8 g (37 mmol), 73.5% of theory; purity: 99.8% according to HPLC. Mixture of two atropisomers according to $^1$H-NMR spectroscopy.

Example 2

2,6-Bis-o-tolyl-9,10-bis(2-(1-methyl-1-phenylethyl)phenyl)-anthracene

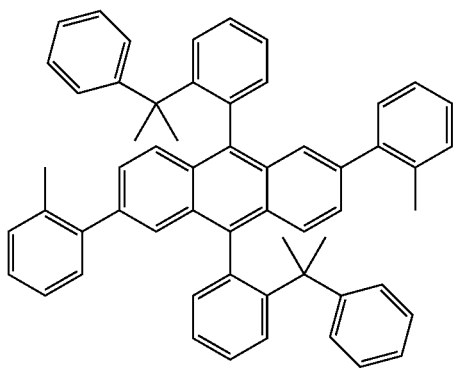 [SMILES: Cc1ccccc1-c1ccc2c(-c3ccccc3C(C)(C)c3ccccc3)c3cc(-c4ccccc4C)ccc3c(-c3ccccc3C(C)(C)c3ccccc3)c2c1]

Procedure analogous to Example 1b. Instead of 18.0 ml (150 mmol) of 2-bromotoluene, 41.3 g (150 mmol) of 1-bromo-2-(1-methyl-1-phenylethyl)benzene are used. Recrystallisation from dioxane. Sublimation p=1×10$^{-5}$ mbar, T=360° C. Yield: 22.6 g (30 mmol), 60.5% of theory; purity: 99.9% according to HPLC. Atropisomerically pure according to $^1$H-NMR spectroscopy.

Example 3

2,6-Bis-o-tolyl-9,10-bis(2-biphenyl)anthracene

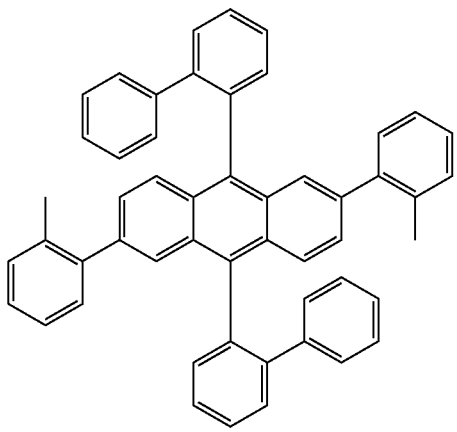 [SMILES: Cc1ccccc1-c1ccc2c(-c3ccccc3-c3ccccc3)c3cc(-c4ccccc4C)ccc3c(-c3ccccc3-c3ccccc3)c2c1]

Procedure analogous to Example 1b. Instead of 18.0 ml (150 mmol) of 2-bromotoluene, 25.9 ml (150 mmol) of 2-bromobiphenyl are used. Recrystallisation from chlorobenzene. Sublimation p=1×10$^{-5}$ mbar, T=360° C. Yield: 27.1 g (41 mmol), 81.7% of theory; purity: 99.9% according to HPLC. Atropisomerically pure according to $^1$H-NMR spectroscopy.

Example 4

2,6-Bis-o-tolyl-9,10-bis(2-trimethylsilylphenyl)anthracene

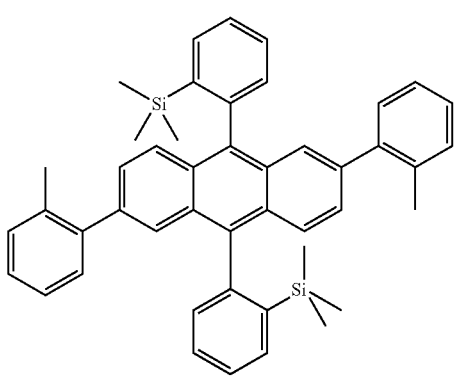 [SMILES: Cc1ccccc1-c1ccc2c(-c3ccccc3[Si](C)(C)C)c3cc(-c4ccccc4C)ccc3c(-c3ccccc3[Si](C)(C)C)c2c1]

Procedure analogous to Example 1b. Instead of 18.0 ml (150 mmol) of 2-bromotoluene, 34.4 g (150 mmol) of 2-trimethylsiylbromobenzene are used. Recrystallisation from dioxane. Sublimation p=1×10$^{-5}$ mbar, T=330° C. Yield: 21.9 g (33 mmol), 66.8% of theory; purity: 99.9% according to HPLC. Atropisomerically pure according to $^1$H-NMR spectroscopy.

Example 5

The following compounds are prepared analogously to Examples 1b, 2, 3 and 4:

| Ex. | Bromide | Product |
|---|---|---|
| 6 | 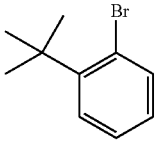 | 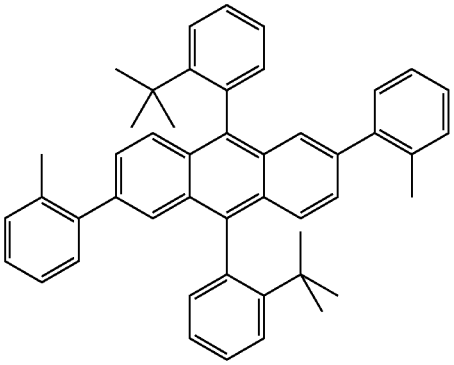 [SMILES: Cc1ccccc1-c1ccc2c(-c3ccccc3C(C)(C)C)c3cc(-c4ccccc4C)ccc3c(-c3ccccc3C(C)(C)C)c2c1] |
| 7 | 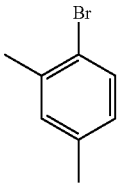 | 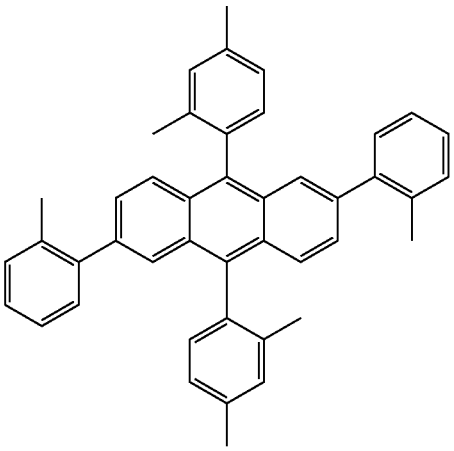 [SMILES: Cc1ccc(-c2c3ccc(-c4ccccc4C)cc3c(-c3ccc(C)cc3C)c3ccc(-c4ccccc4C)cc23)c(C)c1] |
| 8 | 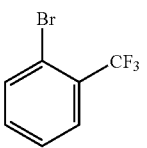 [SMILES: FC(F)(F)c1ccccc1Br] | 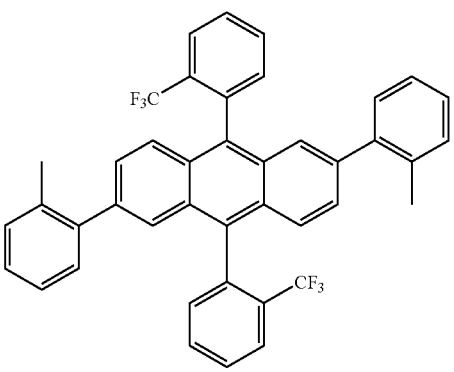 [SMILES: Cc1ccccc1-c1ccc2c(-c3ccccc3C(F)(F)F)c3cc(-c4ccccc4C)ccc3c(-c3ccccc3C(F)(F)F)c2c1] |

-continued
| Ex. | Bromide | Product |
|---|---|---|
| 9 | 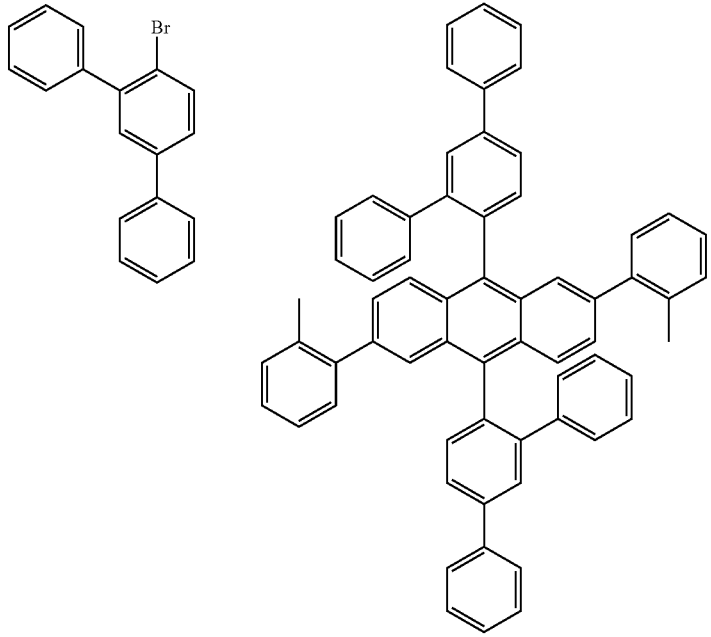 | |
| 10 | 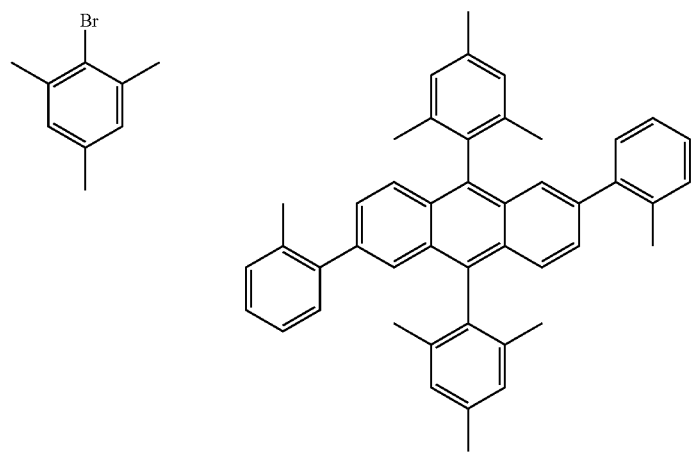 | |

-continued

| Ex. | Bromide | Product |
|---|---|---|
| 11 | | |
| 12 | | |

Example 13

2,6-Bisnaphth-1-yl-9,10-bis-o-tolylanthracene a) 2,6-Bisnaphth-1-ylanthraquinone

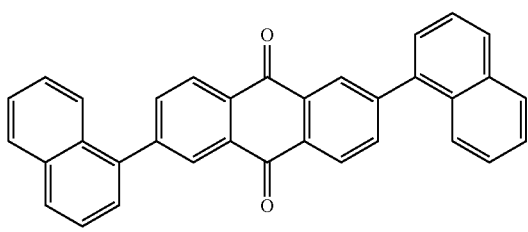 [SMILES: O=C1c2ccc(-c3cccc4ccccc34)cc2C(=O)c2ccc(-c3cccc4ccccc34)cc21]

A suspension of 28.7 g (100 mmol) of 2,6-dibromoanthraquinone, 44.7 g (260 mmol) of 1-naphthylboronic acid, 89.2 g (420 mmol) of potassium phosphate, 1.8 g (6 mmol) of tri-o-tolylphosphine and 225 mg (1 mmol) of palladium(II) acetate in a mixture of 200 ml of dioxane, 400 ml of toluene and 500 ml of water is refluxed for 16 h. After cooling, the solid is filtered off with suction, washed three times with 100 ml of water each time and three times with 100 ml of ethanol each time, dried in vacuo and subsequently recrystallised twice from chlorobenzene. Yield: 41.6 g (90 mmol), 90.3% of theory; purity: 99% according to NMR.

b) 2,6-Bisnaphth-1-yl-9,10-bis-o-tolylanthracene

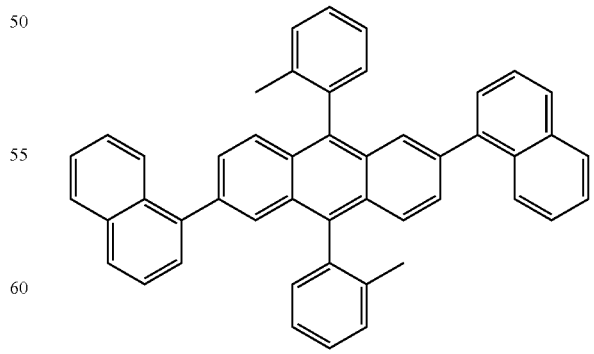

Procedure analogous to Example 1b. Recrystallisation from NMP. Sublimation $p=1\times10^{-5}$ mbar, T=375° C. Yield: 22.2 g (36 mmol), 72.7% of theory; purity: 99.9% according to HPLC. Mixture of two atropisomers according to $^1$H-NMR spectroscopy.

Example 14
The following compounds are prepared analogously to Example 13:
| Ex. | Bromide | Product |
|---|---|---|
| 15 | 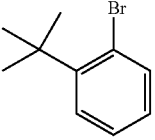 | 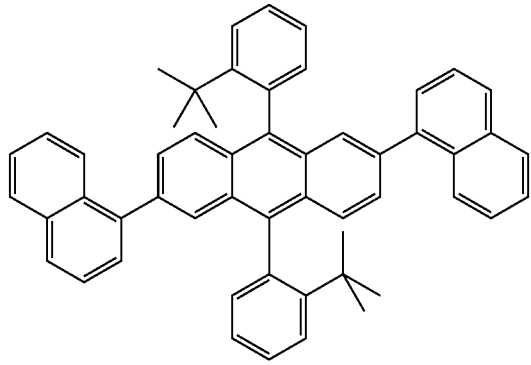 [SMILES: CC(C)(C)c1ccccc1-c1c2ccc(-c3cccc4ccccc34)cc2c(-c2ccccc2C(C)(C)C)c2ccc(-c3cccc4ccccc34)cc12] |
| 16 | 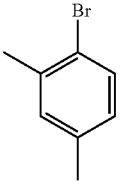 | 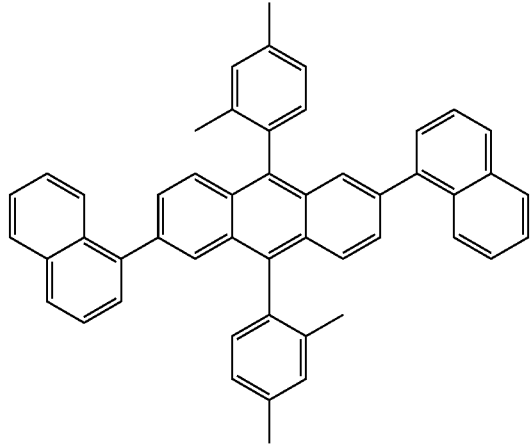 [SMILES: Cc1ccc(-c2c3ccc(-c4cccc5ccccc45)cc3c(-c3ccc(C)cc3C)c3ccc(-c4cccc5ccccc45)cc23)c(C)c1] |
| 17 | 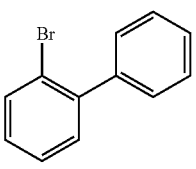 [SMILES: Brc1ccccc1-c1ccccc1] | 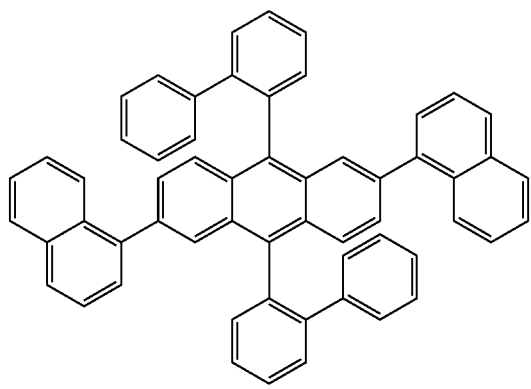 [SMILES: c1ccc(-c2ccccc2-c2c3ccc(-c4cccc5ccccc45)cc3c(-c3ccccc3-c3ccccc3)c3ccc(-c4cccc5ccccc45)cc23)cc1] |

Example 18

2,6-Bis(9-(4-methylnaphthyl)anthracen-10-yl)-9,10-bis-o-tolylanthracene a) 2,6-Bis-(9-(4-methylnaphthyl)anthracen-10-yl)anthraquinone

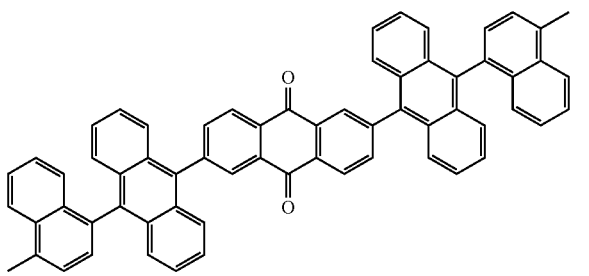 [SMILES: Cc1ccc(-c2c3ccccc3c(-c3ccc4c(c3)C(=O)c3ccc(-c5c6ccccc6c(-c6ccc(C)c7ccccc67)c6ccccc56)cc3C4=O)c3ccccc23)c2ccccc12]

A suspension of 28.7 g (100 mmol) of 2,6-dibromoanthraquinone, 133.3 g (300 mmol) of pinacolyl 10-(4-methylnaphth-1-yl)anthracene-9-boronate, 96.7 g (600 mmol) of potassium fluoride and 1.2 g (1 mmol) of tetrakis-triphenylphosphinopalladium(0) in a mixture of 500 ml of ethylene glycol dimethyl ether, 200 ml of ethanol and 400 ml of water is refluxed for 36 h. After cooling, the solid is filtered off with suction, washed three times with 100 ml of water each time and three times with 100 ml of ethanol each time, dried in vacuo and subsequently recrystallised twice from o-dichlorobenzene. Yield: 66.9 g (79 mmol), 79.5% of theory; purity: 98% according to NMR.

b) 2,6-Bis-(9-(4-methylnaphthyl)anthracen-10-yl)-9,10-bis-o-tolyl-anthracene

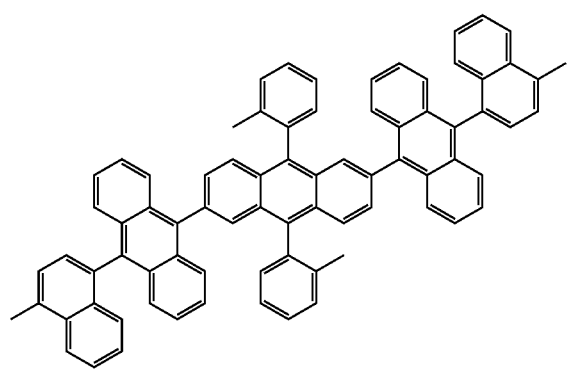

Procedure analogous to Example 1b. Instead of 19.4 g (50 mmol) of 2,6-bis-o-tolylanthraquinone, 42.1 g (50 mmol) of 2,6-bis(9-(4-methylnaphthyl)anthracen-10-yl)anthraquinone are used. After addition of the 2,6-bis(9-(4-methylnaphthyl)anthracen-10-yl)anthraquinone, 300 ml of toluene are added to the reaction mixture. Recrystallisation from o-dichlorobenzene. Sublimation p=1×10$^{-5}$ mbar, T 400° C. Yield: 27.5 g (28 mmol), 55.5% of theory; purity: 99.9% according to HPLC. Mixture of two atropisomers according to $^1$H-NMR spectroscopy.

Example 19

2,6-Bis(p-tolylamino)-9,10-bis-o-tolylanthracene a) 2,6-Dibromo-9,10-bis-o-tolylanthracene

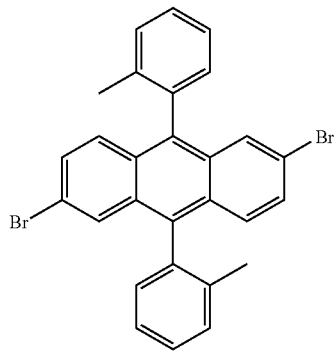 [SMILES: Cc1ccccc1-c1c2ccc(Br)cc2c(-c2ccccc2C)c2ccc(Br)cc12]

Procedure analogous to Example 1b. Instead of 19.4 g (50 mmol) of 2,6-bis-o-tolylanthraquinone, 18.3 g (50 mmol) of 2,6-dibromoanthraquinone are used. Recrystallisation from toluene. Yield: 12.3 g (24 mmol), 47.6% of theory; purity: 97% according to NMR.

b) 2,6-Bis(di-p-tolylaminophenyl-4-yl)-9,10-bis-o-tolylanthracene

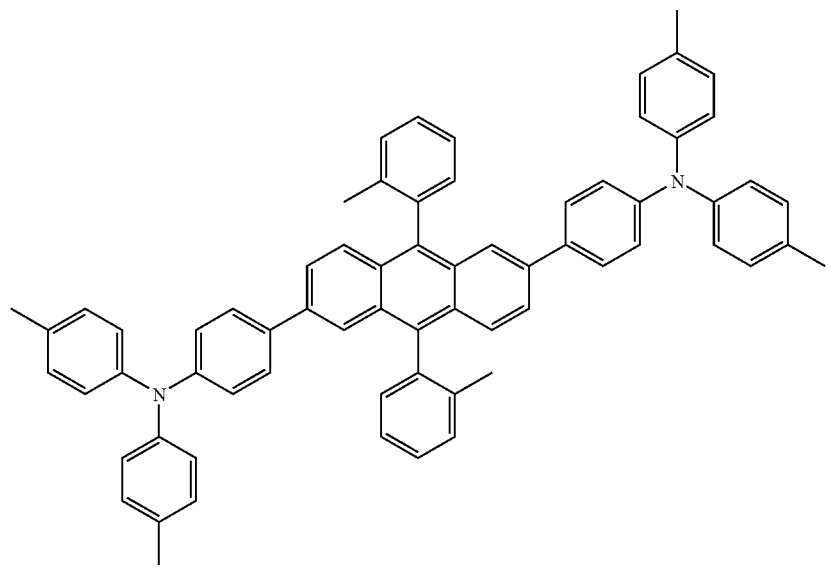

A suspension of 51.6 g (100 mmol) of 2,6-dibromo-9,10-bis-o-tolylanthracene, 82.5 g (260 mmol) of di-p-tolylaminophenyl-4-boronic acid, 89.2 g (420 mmol) of potassium phosphate, 1.8 g (6 mmol) of tri-o-tolylphosphine and 225 mg (1 mmol) of palladium(II) acetate in a mixture of 200 ml of dioxane, 400 ml of toluene and 500 ml of water is refluxed for 16 h. After cooling, the solid is filtered off with suction, washed three times with 100 ml of water each time, washed three times with 100 ml of ethanol each time, dried in vacuo, recrystallised five times from DMF and then sublimed in vacuo (p=1×10⁻⁵ mbar, T=365° C.). Yield: 68.7 g (76 mmol), 76.2% of theory; purity: 99.9% according to HPLC.

Example 20

The following compounds are prepared analogously to Example 19:

| Ex. | Amine | Product |
|---|---|---|
| 21 | | |

| Ex. | Amine | Product |
|---|---|---|
| 22 | | |
| 23 | | |
| 24 | | |

-continued
| Ex. | Amine | Product |
|---|---|---|
| 25 | 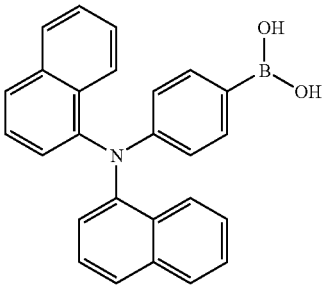 [SMILES: OB(O)c1ccc(N(c2cccc3ccccc23)c2cccc3ccccc23)cc1] | 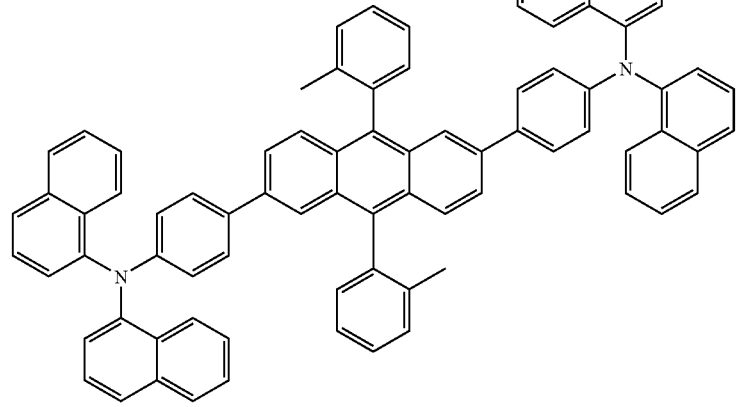 |
| 26 | 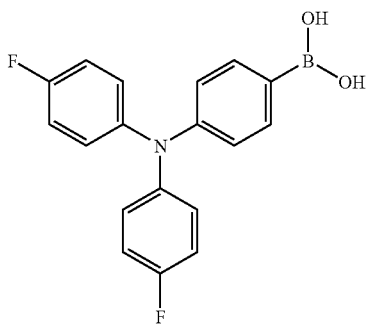 [SMILES: OB(O)c1ccc(N(c2ccc(F)cc2)c2ccc(F)cc2)cc1] | 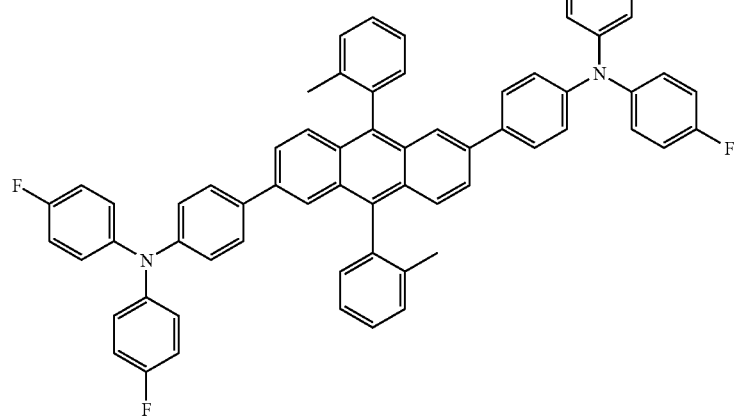 |

| Ex. | Amine | Product |
|---|---|---|
| 27 | | |
| 28 | | |

Example 29

2,6-Bisnaphth-1-yl-9-o-tolyl-10-2-biphenylanthracene

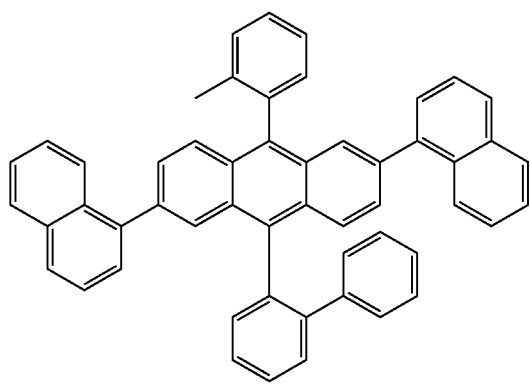 [SMILES: Cc1ccccc1-c1c2cc(-c3cccc4ccccc34)ccc2c(-c2ccccc2-c2ccccc2)c2cc(-c3cccc4ccccc34)ccc12]

A 2-lithiobiphenyl solution in 200 ml of THF, prepared from 11.7 g (50 mmol) of 2-bromobiphenyl and 20 ml (50 mmol) of 2.5N n-butyllithium at −78° C., is added dropwise at −78° C. with vigorous stirring to a suspension of 46.1 g (100 mmol) of 2,6-bisnaphth-1-ylanthraquinone in 500 ml of THF, and the mixture is stirred for a further 30 min. A 2-lithiotoluene solution in THF, prepared from 8.7 g (50 mmol) of 2-bromotoluene and 20 ml (50 mmol) of 2.5 N n-butyllithium at −78° C., is subsequently added to this suspension, and the mixture is stirred for a further 30 min. The reaction mixture is allowed to warm to room temperature, 30 ml of ethanol are added, and the solvent is removed in vacuo. The residue is taken up in 300 ml of DMF and warmed to 60° C., and 17.7 g (130 mmol) of tin(II) chloride are added in portions with vigorous stirring (note: exothermic reaction!). The mixture is subsequently stirred at 60° C. for a further 2 h. After cooling, 500 ml of 2.5 N hydrochloric acid are added, and the solid is filtered off with suction. The solid is washed three times with 100 ml of 2.5 N hydrochloric acid each time, three times with 100 ml of water each time and three times with 100 ml of ethanol each time, dried in vacuo and subsequently recrystallised once from acetic acid and three times from dioxane.

Sublimation p=1×10⁻⁵ mbar, T=345° C. Yield: 43.1 g (64 mmol), 64.0% of theory; purity: 99.9% according to HPLC. Mixture of two atropisomers according to ¹H-NMR spectroscopy.
Example 30
The following compounds are prepared analogously to Example 29:
| Ex. | Bromides | Product |
|---|---|---|
| 31 | 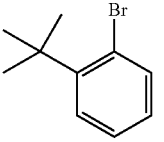 | 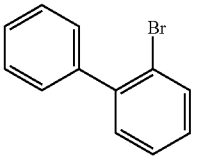 [SMILES: Brc1ccccc1-c1ccccc1] |
| 32 | 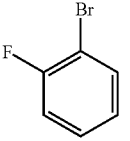 | 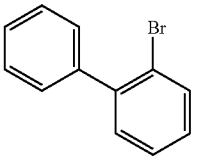 [SMILES: Brc1ccccc1-c1ccccc1] |
| 33 | 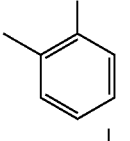 | 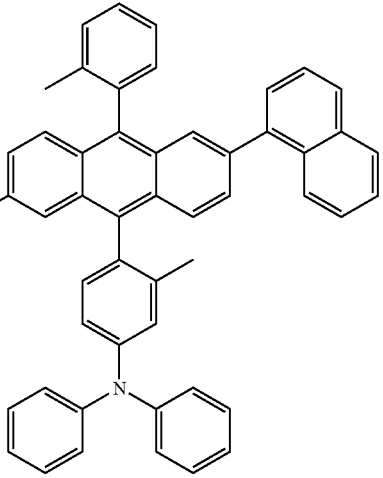 |

| Ex. | Bromides | Product |
|---|---|---|
| 34 | | |

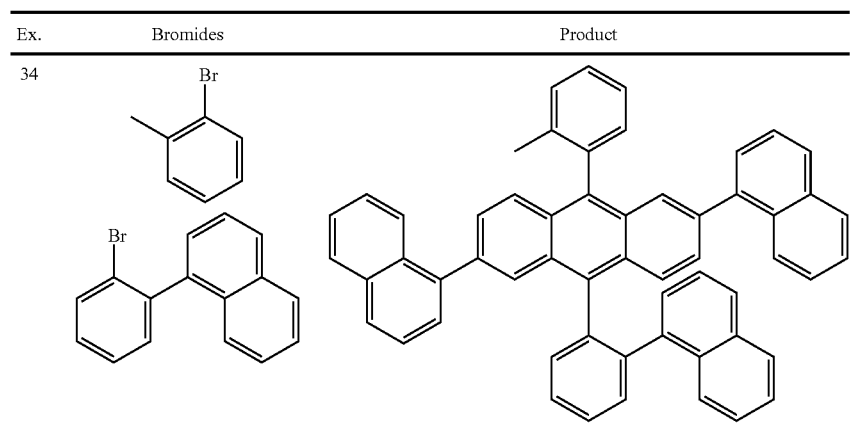

Example 35

Production of OLEDs

OLEDs are produced by a general process as described in WO 04/058911, which is adapted in individual cases to the particular circumstances (for example layer-thickness variation in order to achieve optimum efficiency or colour).

The results for various OLEDs are presented in Examples 36 to 48 below. Glass plates coated with structured ITO (indium tin oxide) form the substrates of the OLEDs. For improved processing, PEDOT (spin-coated from water; purchased from H. C. Starck, Goslar, Germany; poly(3,4-ethylene-dioxy-2,5-thiophene)) is applied directly to the substrate. The OLEDs always consist of the following layer sequence: substrate/PEDOT 20 nm/hole-injection layer (HIL1) 20 nm/hole-transport layer (HTM1) 20 nm/emission layer (EML) 30 nm/electron-transport layer (ETM1) 20 nm and finally a cathode. The materials apart from PEDOT are thermally vapour-deposited in a vacuum chamber. The EML here always consists of a matrix material (host) and a dopant (guest), which is admixed with the host by co-evaporation. The cathode is formed by a 1 nm thin LiF layer and a 150 nm Al layer deposited on top. Table 2 shows the chemical structures of the materials used to construct the OLEDs.

These OLEDs are characterised by standard methods; for this purpose, the electroluminescence spectra, the efficiency (measured in cd/A), the power efficiency (measured in lm/W) as a function of the brightness, calculated from current/voltage/luminance characteristics (IUL characteristics), and the lifetime are determined +. The lifetime is defined as the time after which the initial luminance has dropped from 1000 cd/m² to half.

Table 3 shows the results for some OLEDs (Examples 36 to 48). The comparative example used is host H1 in accordance with the prior art.

TABLE 2

Compounds used

HIL1

TABLE 2-continued

Compounds used

HTM1

ETM1

H1 (comparison)

D1

TABLE 2-continued

Compounds used

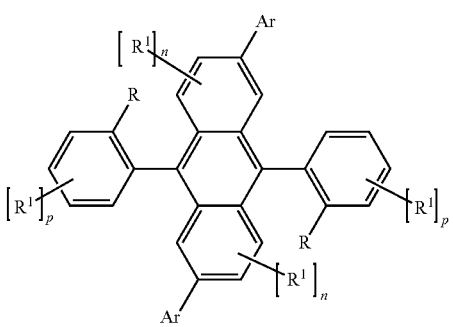

D2

TABLE 3

OLED results

| Example | EML | Max. efficiency (cd/A) | Voltage (V) at 1000 cd/m² | CIE | Lifetime (h) at 1000 cd/m² |
|---|---|---|---|---|---|
| 36 (comparison) | H1 + 5% D1 | 9.9 | 5.7 | x = 0.17/y = 0.33 | 4050 |
| 37 (comparison) | H1 + 5% D2 | 3.4 | 6.2 | x = 0.15/y = 0.13 | 1200 |
| 38 | Ex. 1 + 5% D1 | 10.5 | 5.5 | x = 0.17/y = 0.33 | 6100 |
| 39 | Ex. 1 + 5% D2 | 3.8 | 5.8 | x = 0.15/y = 0.14 | 1800 |
| 40 | Ex. 3 + 5% D1 | 12.2 | 5.7 | x = 0.17/y = 0.33 | 5800 |
| 41 | Ex. 3 + 5% D2 | 4.2 | 5.9 | x = 0.15/y = 0.14 | 1600 |
| 42 | Ex. 9 + 5% D2 | 11.3 | 5.4 | x = 0.17/y = 0.32 | 6300 |
| 43 | Ex. 9 + 5% D2 | 3.9 | 5.8 | x = 0.15/y = 0.15 | 2200 |
| 44 | Ex. 17 + 5% D3 | 11.5 | 5.5 | x = 0.17/y = 0.33 | 7100 |
| 45 | Ex. 17 + 5% D3 | 3.5 | 5.9 | x = 0.15/y = 0.14 | 2000 |
| 46 | Ex. 9 + 5% Ex. 11 | 7.8 | 5.3 | x = 0.15/y = 0.19 | 4800 |
| 47 | Ex. 9 + 5% Ex. 19 | 8.0 | 5.6 | x = 0.15/y = 0.24 | 5300 |
| 48 | Ex. 17 + 7% Ex. 19 | 8.3 | 5.3 | x = 0.16/y = 0.26 | 5600 |

The invention claimed is:

1. A compound of formula (1)

Formula (1)

wherein

Ar is, identically or differently on each occurrence, phenyl, 1-naphthyl, 2-naphthyl, 2-anthryl, 9-anthryl, 2-phenanthrenyl, 3-phenanthrenyl or 9-phenanthrenyl each optionally substituted by one or more radicals R';

R is, identically on each occurrence, F, $Si(R^2)_3$; $-N(Ar^1)_2$; a straight-chain alkyl or alkoxy group having 1 to 4 C atoms or a branched alkyl group having 3 to 5 C atoms, each of which may be substituted by one or more radicals $R^2$, where one or more H atoms may be replaced by F, or a phenyl group;

$R^1$ are, identically or differently on each occurrence, F; Cl; Br; I; CN; $N(Ar^1)_2$; $C(=O)Ar^1$; $P(Ar^1)_2$; $P(=O)(Ar^1)_2$; $Si(R^2)_3$; $NO_2$; a straight-chain alkyl, alkoxy or thioalkoxy group having 1 to 40 C atoms optionally substituted by one or more radicals $R^2$; or a branched or cyclic alkyl, alkoxy or thioalkoxy group having 3 to 40 C atoms optionally substituted by one or more radicals $R^2$; wherein one or more non-adjacent $CH_2$ groups of said straight-chain alkyl, alkoxy or thioalkoxy group or said branched or cyclic alkyl, alkoxy or thioalkoxy group are optionally replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-O-$, —S—, —N(R$^2$)—, or —CONR$^2$— and wherein one or more H atoms of said straight-chain alkyl, alkoxy or thioalkoxy group or said branched or cyclic alkyl, alkoxy or thioalkoxy group are optionally replaced by F, Cl, Br, I, CN, or NO$_2$; an aromatic or hetero-aromatic ring system having 5 to 30 aromatic ring atoms optionally substituted by one or more radicals R$^2$; or an aryloxy or heteroaryloxy group having 5 to 24 aromatic ring atoms optionally substituted by one or more radicals R$^2$; or a combination of two, three, four or five substituents R$^1$;

Ar$^1$ is, identically or differently on each occurrence, an aromatic or heteroaromatic ring system having 5 to 30 aromatic ring atoms optionally substituted by one or more non-aromatic radicals R$^1$ and wherein two radicals Ar$^1$ are optionally connected to one another by a single bond or an O, S, N(R$^2$), or C(R$^2$)$_2$ group;

R$^2$ is, identically or differently on each occurrence, H or a hydrocarbon radical having 1 to 20 C atoms, wherein said hydrocarbon radical is aliphatic, aromatic, or a combination of aliphatic and aromatic and is optionally substituted by F and wherein two or more radicals R$^2$ optionally define a mono- or polycyclic, aliphatic or aromatic ring system with one another;

n is 0;
p is 0;
with the proviso that if R$^1$ contains a benzimidazole group, it is not bonded to Ar.

2. The compound of claim 1, wherein both Ar are identical.

3. The compound of claim 1, wherein said compound has a formula selected from the group consisting of formulae (2), (3), (4), and (5)

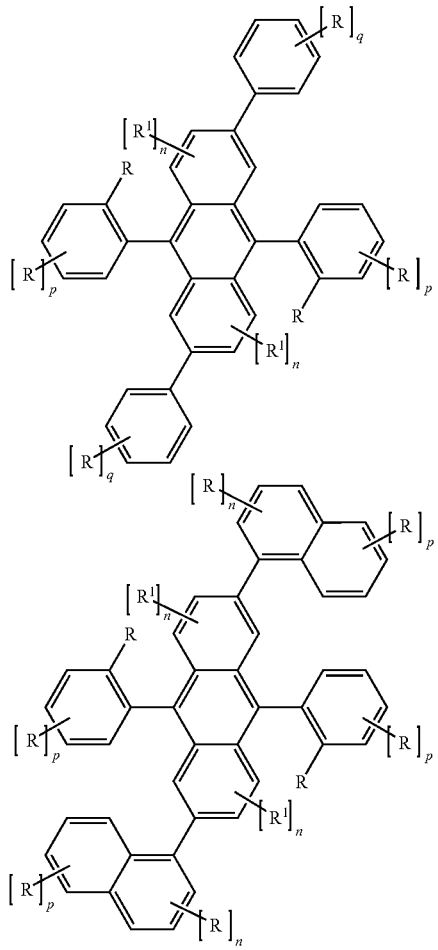

Formula (2)

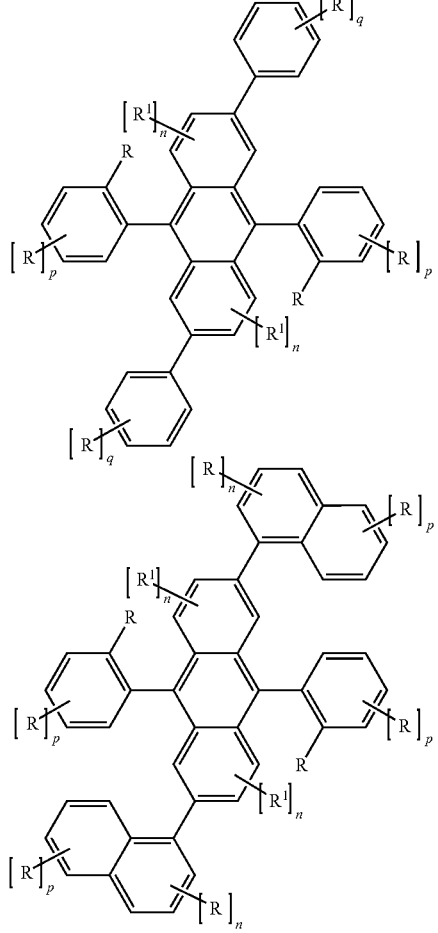

Formula (3)

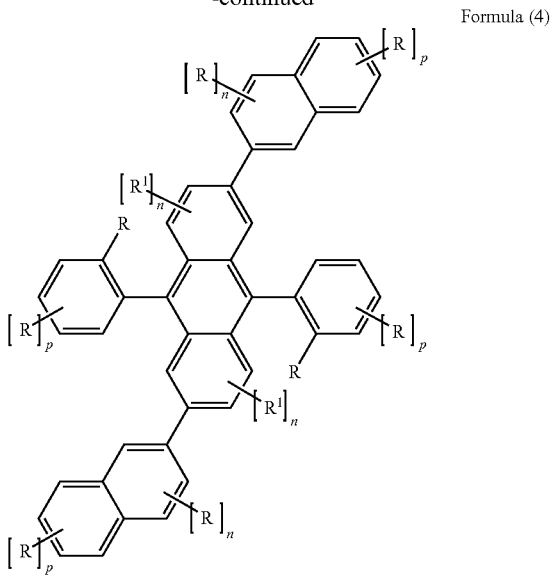

Formula (4)

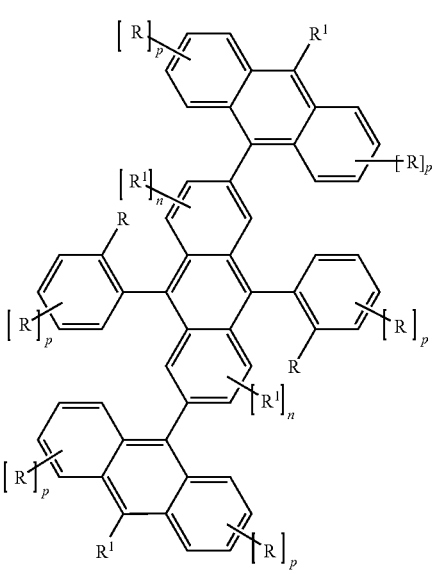

Formula (5)

wherein q is 0, 1, 2, 3, 4, or 5.

4. A process for preparing the compound of claim 1 comprising (1) reacting an anthraquinone substituted in the 2,6-position by chlorine, bromine, iodine, or a sulfonic acid derivative with a boronic acid derivative of the group Ar with palladium catalysis to form a first intermediate, (2) reacting said first intermediate with a corresponding ortho-substituted organometallic phenyl derivative to form a second intermediate, and (3) reducing said second intermediate.

5. An organic electronic device selected from the group consisting of organic electroluminescent devices, organic field-effect transistors, organic thin-film transistors, organic light-emitting transistors, organic integrated circuits, organic solar cells, organic field-quench devices, organic photo receptors, light-emitting electrochemical cells and organic laser diodes, comprising at least one compound of claim 1.

6. An organic electroluminescent device comprising at least one compound of claim 1.

7. The organic electroluminescent device of claim 6, comprising an anode, a cathode, and at least one emitting layer, and optionally comprising further layers selected from the group consisting of hole-injection layers, hole-transport layers, hole-blocking layers, electron-transport layers, electron-injection layers, and/or charge-generation layers.

8. The organic electroluminescent device of claim 7, wherein said organic electroluminescent device comprises a host material comprising a host and a dopant wherein said host material comprises the compound of claim 1 and is used as a fluorescent emitter and/or as an electron-transport material and/or as a hole-blocking material.

9. The organic electroluminescent device of claim 8, wherein said dopants are selected from the group consisting of aromatic anthraceneamines, aromatic anthracenediamines, aromatic pyreneamines, aromatic pyrenediamines, monostyrylamines, distyrylamines, tristyrylamines, tetrastyrylamines, styrylphosphines, styryl ethers, and arylamines.

10. The organic electroluminescent device of claim 7, wherein said compound of claim 1 is used as an emitting compound in an emitting layer and/or as a hole-transport material.

11. The organic electroluminescent device of claim 10, wherein said hole-transport material is comprised in a hole-transport layer or a hole-injection layer.

12. The organic electroluminescent device of claim 11, wherein R is an N(Ar$^1$)$_2$ group and/or R$^1$ is an N(Ar$^1$)$_2$ group.

13. The compound of claim 1, wherein Ar is a group of Formula (9), Formula (10) or Formula (11)

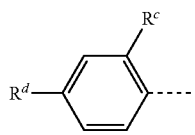

Formula (9)

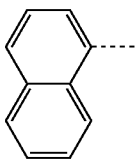

Formula (10)

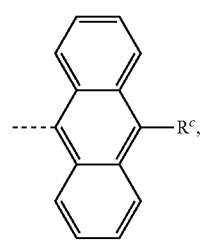

Formula (11)

wherein R$^c$ and R$^d$ are defined as R$^1$, with the proviso that R$^c$ in Formula (9) is defined as R.

14. The compound of claim 1, wherein R is, identically or differently on each occurrence, F, Si(R$^2$)$_3$, a straight-chain alkyl or alkoxy group having 1 to 4 C atoms or a branched alkyl group having 3 to 5 C atoms, each of which may be substituted by one or more radicals R$^2$, where one or more H atoms may be replaced by F.

* * * * *